(12) United States Patent
Lure et al.

(10) Patent No.: US 12,373,947 B2
(45) Date of Patent: Jul. 29, 2025

(54) SYSTEM AND METHOD FOR DETECTING LUNG ABNORMALITIES

(71) Applicant: SHENZHEN SMART IMAGING HEALTHCARE CO., LTD., Guangdong (CN)

(72) Inventors: Fleming Yuan-Ming Lure, Potomac, MD (US); Shenwen Quan, Shenzhen (CN); Hao Zhou, Shenzhen (CN); Kunlei Hong, Shenzhen (CN); Qian Xiao, Shenzhen (CN); Lingjun Qian, Shenzhen (CN)

( * ) Notice: Subject to any disclaimer, the term of this patent is extended or adjusted under 35 U.S.C. 154(b) by 374 days.

(21) Appl. No.: 18/155,752

(22) Filed: Jan. 18, 2023

(65) Prior Publication Data

US 2023/0230241 A1   Jul. 20, 2023

Related U.S. Application Data

(60) Provisional application No. 63/303,982, filed on Jan. 27, 2022.

(30) Foreign Application Priority Data

Jan. 18, 2022 (CN) .......................... 202210052786.6

(51) Int. Cl.
*G06K 9/00* (2022.01)
*G06T 7/00* (2017.01)
*G06T 7/11* (2017.01)

(52) U.S. Cl.
CPC .............. *G06T 7/0012* (2013.01); *G06T 7/11* (2017.01); *G06T 2207/20081* (2013.01); *G06T 2207/30061* (2013.01)

(58) Field of Classification Search
CPC ................... G06T 7/0012; G06T 7/11; G06T 2207/20081; G06T 2207/30061; G06T 2207/10081; G06T 2207/10088; G06T 2207/20016; G06T 2207/20076; G06T 2207/10116; G06T 2207/20084; G06T 2207/20132; G06T 2207/30064; G06T 2207/30096; G16H 30/20; G16H 30/40; G16H 50/20; G16H 50/30; G16H 50/70; G16H 15/00
See application file for complete search history.

(56) References Cited

U.S. PATENT DOCUMENTS

| | | | | |
|---|---|---|---|---|
| 7,236,619 B2 * | 6/2007 | Doi | ........................ | G06T 7/0012 382/128 |
| 7,935,055 B2 * | 5/2011 | Burckhardt | ............ | A61B 6/032 600/300 |
| 10,692,211 B2 * | 6/2020 | Madabhushi | ........... | G06T 15/08 |
| 11,551,353 B2 * | 1/2023 | Golden | .................. | G16H 70/20 |

(Continued)

*Primary Examiner* — Shervin K Nakhjavan

(57) ABSTRACT

A computer-implemented method for detecting lung abnormalities is provided. The method includes the steps of: acquiring a chest image of a subject; labeling one or more regions of interest (ROIs) in the chest image; segmenting a fine-grained boundary of each of the labeled ROIs; generating a plurality of output matrixes for each of the segmented ROIs; sorting a plurality of prediction scores obtained in the output matrixes, and generating a plurality of recommendations of potential abnormalities for each of the ROIs; and outputting the recommendations, A smart imagery framing and truthing (SIFT) system for implementing the method is also provided.

17 Claims, 30 Drawing Sheets

(56) References Cited

U.S. PATENT DOCUMENTS

| | | | |
|---|---|---|---|
| 11,810,291 B2* | 11/2023 | Liu | G06T 7/11 |
| 11,935,234 B2* | 3/2024 | Kondo | A61B 6/00 |
| 11,967,072 B2* | 4/2024 | Xie | G06T 7/10 |
| 2021/0398654 A1* | 12/2021 | Chaganti | G16H 50/80 |
| 2023/0033075 A1* | 2/2023 | Xu | G06V 10/82 |
| 2023/0059426 A1* | 2/2023 | Liu | G06T 7/73 |

* cited by examiner (a) Radiologist only (2 weeks ago)

(b) SIFT only (2 weeks later)

(c) Radiologist using SIFT (2 weeks later)

| ROI labelled by Radiologists | True Positive ROI | | | False Positive ROI | | |
|---|---|---|---|---|---|---|
| | Consensus | No Consensus | Sub-total | Consensus | No Consensus | Sub-total |
| Without SIFT assistance | 201 | 26 | 227 | 65 | 78 | 143 |
| With SIFT assistance | 211 | 28 | 239 | 47 | 60 | 107 |
| Change of labelled ROI | 5.00% | 7.69% | 5.29% | -27.70% | -23.08% | -25.17% |
| P value | | P=0.16 | | | P<0.001 | |

FIG. 27

| Review time (second) | Radiologist 1 | Radiologist 2 | Radiologist 3 | Average |
|---|---|---|---|---|
| Without SIFT assistance | 63.08 | 72.53 | 56.1 | 63.90 |
| With SIFT assistance | 30.48 | 47.17 | 32.9 | 36.85 |
| Improvement (%) | 51.68% | 34.96% | 41.35% | 42.33% |

FIG. 28

| | Measures (Average) | Without SIFT assistance | With SIFT assistance | Changes | P value |
|---|---|---|---|---|---|
| Consistency | STDEV of annotated area | 8,464,316 | 6,074,638 | -28.23% | P<0.001 |
| | Consensus area (IOU) | 0.629 | 0.762 | 25.27% | P<0.001 |
| | Consensus labelled abnormalities | | | | |
| | Number of consensus TP | 201 | 211 | 5.00% | P<0.001 |
| | Number of consensus FP | 65 | 47 | -27.73% | P<0.001 |
| Efficiency | Average time to annotate single image (s) | 63.90 | 36.85 | 42.33% | P<0.001 |
| Accuracy | Average AUC | 0.857 | 0.873 | 0.016 | P<0.001 |

SYSTEM AND METHOD FOR DETECTING LUNG ABNORMALITIES

CROSS-REFERENCE TO RELATED APPLICATION

This non-provisional patent application claims the benefit of U.S. provisional patent application No. 63/303,982, filed on Jan. 27, 2022, and claims priority to China Patent Application No. 202210052786.6, filed on Jan. 18, 2022, the contents of which are incorporated herein by reference in their entirety.

BACKGROUND

Technical Field

The present disclosure relates to a method for detecting lung abnormalities, more particularly to a computer-implemented method for detecting multiple lung abnormalities and a system for implementing the same.

Related Art

Chest X-ray radiography (CXR) is a commonly used medical imaging modality to screen and detect a variety of lung diseases or abnormalities (e.g., lung nodules, tuberculosis, pneumonia, etc.) in current clinical practice due to its wide accessibility and low cost. However, due to the subtleness of many early lung disease patterns or abnormalities depicted on the two-dimensional X-ray projection images and large reading volume in the busy clinical practice, accurately reading and interpreting chest X-ray images by the general radiologists is often tedious and difficult, which results in significant detection or diagnosis errors and large inter-reader variability. For example, a previous study reported that 22% of all errors in diagnostic radiology were made in reading CXR images and another study reported low inter-reader agreement with Cohen's kappa coefficients ranging from 0.25 to 0.52 among eight radiologists to detect tuberculosis in an HIV-positive cohort of 139 CXR images. In addition, interpreting CXR images is also a time-consuming task, with 15% to 25% of the time spent on image interpretation, and the remaining time (75% to 85%) on writing the diagnostic report. For abnormal cases, the radiological report requires a description of the location for different abnormalities. The shortage of experienced or well-trained radiologists in many healthcare systems worldwide drives an increase in demand for CXR readings. Thus, it is highly desired to develop and implement an automated or semi-automated tool that enables radiologists more accurately detect lung diseases and efficiently generate diagnosis reports, which may play an important role to improve radiologists' productivity or efficiency in the busy clinical workflow.

In order to help address the clinical challenges and reduce diagnostic errors in reading and interpreting CXR images, developing computer-aided detection or diagnosis (CAD) schemes of CXR images using either conventional medical image processing algorithms or artificial intelligence (AI) technologies have been attracting broad research interest in the last several decades. As a result, researchers have developed different CAD schemes to automatically detect pulmonary diseases such as tuberculosis, lung nodule and pneumonia using CXR images and reported decent performance compared to radiologists in the reported studies. Clinical evaluation studies have also been reported recently to assess potential clinical use of CAD schemes for CXR images.

However, existing CAD of CXR images still have several major limitations. (1) In clinical practice, different types of lung abnormalities or disease patterns may depict on a single CXR image and radiologists detect and diagnose multiple diseases in reading and interpreting this single CXR image at the same time. However, current CAD schemes are typically single task detection schemes that are developed or trained to only detect or diagnose a single specific disease depicted on CXR images (including the new schemes to detect COVID-19 infected pneumonia). Thus, the potentially clinical utility of applying existing CAD schemes of CXR images is limited. (2) Most current CAD schemes use a "black-box" type approach that only generates a simple binary decision for each CXR image to predict the possibility of having a specific type of abnormality without annotating the central location and/or the segmented boundary contour of the abnormality, which is critical for physicians to have higher confidence to accept CAD-generated results and more accurately diagnose abnormality and its severity. (3) Current CAD schemes do not include a function or capability to automatically generate a draft of a diagnostic report or provide the standard information that can help improve the efficacy of radiologists to write the final diagnostic report, which is often a quite time-consuming task.

SUMMARY

To overcome the limitations of existing CAD schemes, the present disclosure provides an innovative AI-based CAD approach that has unique characteristics, including: (1) it detects multiple lung abnormalities if they exist on one CXR image, (2) it includes a visual aid tool or graphic user interface to provide automated annotation of abnormality location and boundary contours, (3) it also automatically generates a draft of a diagnostic report that includes the standard medical terms to describe all detected abnormalities, their locations and severity for radiologists to accept the report or make any necessary minor modification with ease.

An embodiment of the present disclosure provides a computer-implemented method for detecting lung abnormalities including the following steps:
  S1: acquiring a chest image of a subject;
  S2: labeling one or more regions of interest (ROIs) in the chest image;
  S3: segmenting a fine-grained boundary of each of the labeled ROIs;
  S4: generating a plurality of output matrixes for each of the segmented ROIs;
  S5: sorting a plurality of prediction scores obtained in the output matrixes, and generating a plurality of recommendations of potential abnormalities for each of the ROIs; and
  S6: outputting the recommendations.

Preferably, the method for detecting lung abnormalities is implemented by a smart imagery framing and truthing (SIFT) system. The SIFT system includes augmented mask regions with a convolutional neural network (Mask R-CNN) and a multi-layer perception neural network (MLPNN) coupled to the Mask R-CNN. The Mask R-CNN includes a Feature Pyramid Network (FPN) for feature extraction, a Region Proposal Network (RPN) coupled to the FPN and for region proposals creation, and an ROI Network coupled to the FPN and the RPN and for box and mask prediction. The MLPNN includes a Data Fusion Center (DFC) for fusing the output matrixes to improve accuracy of the prediction scores, a Max-Predictive Network (MPN) coupled to the DFC and for determining abnormalities having a maximum prediction score, and an Optimal Recommendation Network (ORN) coupled to the DFC and the MPN and for generating additional recommendations.

Preferably, the FPN splits a feature map from a channel dimension, convolves the feature map to generate a plurality of sub feature maps, concatenates and adds the generated sub feature maps, weighting the added sub feature maps to obtain a weighted feature map.

Preferably, the added sub features maps are weighted according to the following steps: performing global pooling on an unweighted feature map to obtain a one-dimensional tensor containing global information; applying the one-dimensional tensor to two fully connected layers to obtain an attention tensor having a length identical to that of the one-dimensional tensor; activating a softmax function to convert the attention tensor into a probability distribution; weighting the unweighted feature map according to the probability distribution; and outputting the weighted feature map.

Preferably, the RPN adopts a first focal loss function for reducing class imbalance and improving prediction accuracy of difficult samples in region proposal creation. The first focal loss function is represented by Equation I: FL(pt)=−(1−pt)^γ×log(pt), wherein pt is a probability of correct prediction, and γ is a hyperparameter for controlling shapes of the focal loss function.

Preferably, the RPN is trained by randomly selecting a predetermined number of anchor boxes matched to each ground truth (GT) box as positive samples, thereby ensuring that samples with large ROI areas and samples with small ROI areas have equal chances to be matched as positive samples.

Preferably, the ROI Network adopts a second focal loss function for reducing class imbalance and improving accuracy of bounding box coordination and segmentation in box and mask prediction. The second focal loss function is represented by Equation II: FL(pt)=−(1−pt)^γ×log(pt)×gtweight, wherein pt is a probability of correct prediction, γ is a hyperparameter for controlling shapes of the focal loss function, and gtweight is an array of weights assigned to each of the potential abnormalities.

Preferably, the ROI Network is trained by randomly selecting a predetermined number of positive sample proposals for each ground truth (GT) box, thereby ensuring that samples with large ROI areas and samples with small ROI areas have equal chances to be matched as positive samples.

Preferably, the MLPNN is fine-tuned with error back-propagation learning for updating weights to improve prediction accuracy.

Preferably, Step S5 includes the following steps:
S5.1: fusing the output matrixes, each of which comprises the prediction scores $S_j$, each of the prediction scores is associated with one potential abnormality, wherein $0 \leq S_j \leq 1$, j=1,2, . . . , n, n is a positive integer;
S5.2: sorting the prediction scores in each of the output matrixes;
S5.3: selecting the output matrix having prediction scores greater than a prediction threshold;
S5.4: generating the recommendations of potential abnormalities according to the selected output matrix.

Preferably, Step S5 further includes the following steps: when one of the ROI is overlapped by more than 30% in area by another ROI, merging the boundaries of the two ROIs; selecting, between the two ROIs, a higher prediction score associated with each potential abnormality; adjusting the selected prediction score according to Equation III; and generating the recommendations according to the adjusted prediction score, $$S = \begin{cases} \frac{\text{score}}{T} * 0.5 & \text{score} \leq T \\ \frac{\text{score} - T}{T} * 0.5 + 0.5 & \text{score} > T \end{cases} \quad \text{(III)}$$

wherein T represents an optimal threshold.

Preferably, the step S2 is performed in response to a user's input.

Preferably, the chest image comprises a plurality of image layers, and the Step S3 further includes the following steps:
S3.1 defining the image layer having the segmented boundary as a first base layer;
S3.2 determining lesion features within the segmented boundary;
S3.3 detecting two image layers immediately adjacent to the first base layer and having the lesion features;
S3.4 segmenting regions having the lesion features in the adjacent image layers;
S3.5 defining at least one of the adjacent image layers as a second base layer; and
S3.6 repeating the Steps S3.2 through S3.4 until the lesion features are no longer detected in the adjacent image layers.

Preferably, the method of detecting lung abnormalities further includes the following steps: receiving a user's selection of one or more of the generated recommendations; and concatenating semantic expressions associated with the selected recommendations to generate a diagnostic report.

Preferably, the method of detecting lung abnormalities further includes the following steps: constructing a knowledge tree module associated with image features of various lung abnormalities; obtaining image descriptions and conclusions of each of the ROIs; and concatenating the image descriptions and conclusions according to the knowledge tree module.

Another embodiment of the present disclosure provides a smart imagery framing and truthing (SIFT) system for detecting lung abnormalities. The SIFT system includes a memory, and at least one processor coupled to the memory. The memory has a computer program stored therein. When the computer program is executed, the processor is controlled to perform the steps of:
S1: acquiring a chest image of a subject;
S2: labeling one or more regions of interest (ROIs) in the chest image;
S3: segmenting a fine-grained boundary of each of the labeled ROIs;
S4: generating a plurality of output matrixes for each of the segmented ROIs;
S5: sorting a plurality of prediction scores obtained in the output matrixes, and generating a plurality of recommendations of potential abnormalities for each of the ROIs; and
S6: outputting the recommendations.

Yet another embodiment of the present disclosure provides a non-transitory computer-readable medium for detecting lung abnormalities. The non-transitory computer-readable medium includes a computer program stored therein. When the computer program is executed, a device installing the non-transitory computer-readable medium is controlled to perform the steps of:

S1: acquiring a chest image of a subject;
S2: labeling one or more regions of interest (ROIs) in the chest image;
S3: segmenting a fine-grained boundary of each of the labeled ROIs;
S4: generating a plurality of output matrixes for each of the segmented ROIs;
S5: sorting a plurality of prediction scores obtained in the output matrixes, and generating a plurality of recommendations of potential abnormalities for each of the ROIs; and
S6: outputting the recommendations.

Preferably, the SIFT system is trained according to the steps of: determining the prediction score of an input image; and if the prediction score is greater than current accuracy of the Mask R-CNN, including, the input image into training dataset of the SIFT system, or if the prediction score is smaller than the current accuracy of the Mask R-CNN, re-training the SIFT system using the input image with correct annotations. The training approach enables the SIFT system to annotate millions pieces of case data with high accuracy. Over 70% of the annotations need not be corrected or modified manually.

In view of the foregoing embodiments, the method for detecting lung abnormalities of the present disclosure and the smart imagery framing and truthing (SIFT) system for implementing the same increase the convenience of physician's reading of CXR images, reduces the time spent by radiologists in quantifying and analyzing pulmonary lesions and prepare diagnostic reports, and facilitates standardization, structuring and electronization of pulmonary abnormalities diagnostic reports. As compared with existing CXR image diagnostic technology, the AI-based CAD approach of the present disclosure utilize different models for classification and segmentation and different data annotation processes, and adopts human-machine cooperation of multi-threshold combination judgment to improve prediction accuracy. In addition, the present disclosure introduces a decision fusion neural network for analyzing potential classification recommendations, and generates diagnostic drafts by a knowledge tree-structured module to facilitate preparation of diagnostic reports by radiologists.

BRIEF DESCRIPTION OF THE DRAWINGS

FIG. 27 shows radiologists' consensus in labeling ROI with and without assistance of the SIFT system in accordance with an embodiment of the present disclosure;

FIG. 28 shows radiologists' annotation time with and without assistance of the SIFT system in accordance with an embodiment of the present disclosure; and FIG. 29 shows a summary of radiologists' performance with and without assistance of the SIFT system in accordance with an embodiment of the present disclosure.

DETAILED DESCRIPTION

Figure 1:
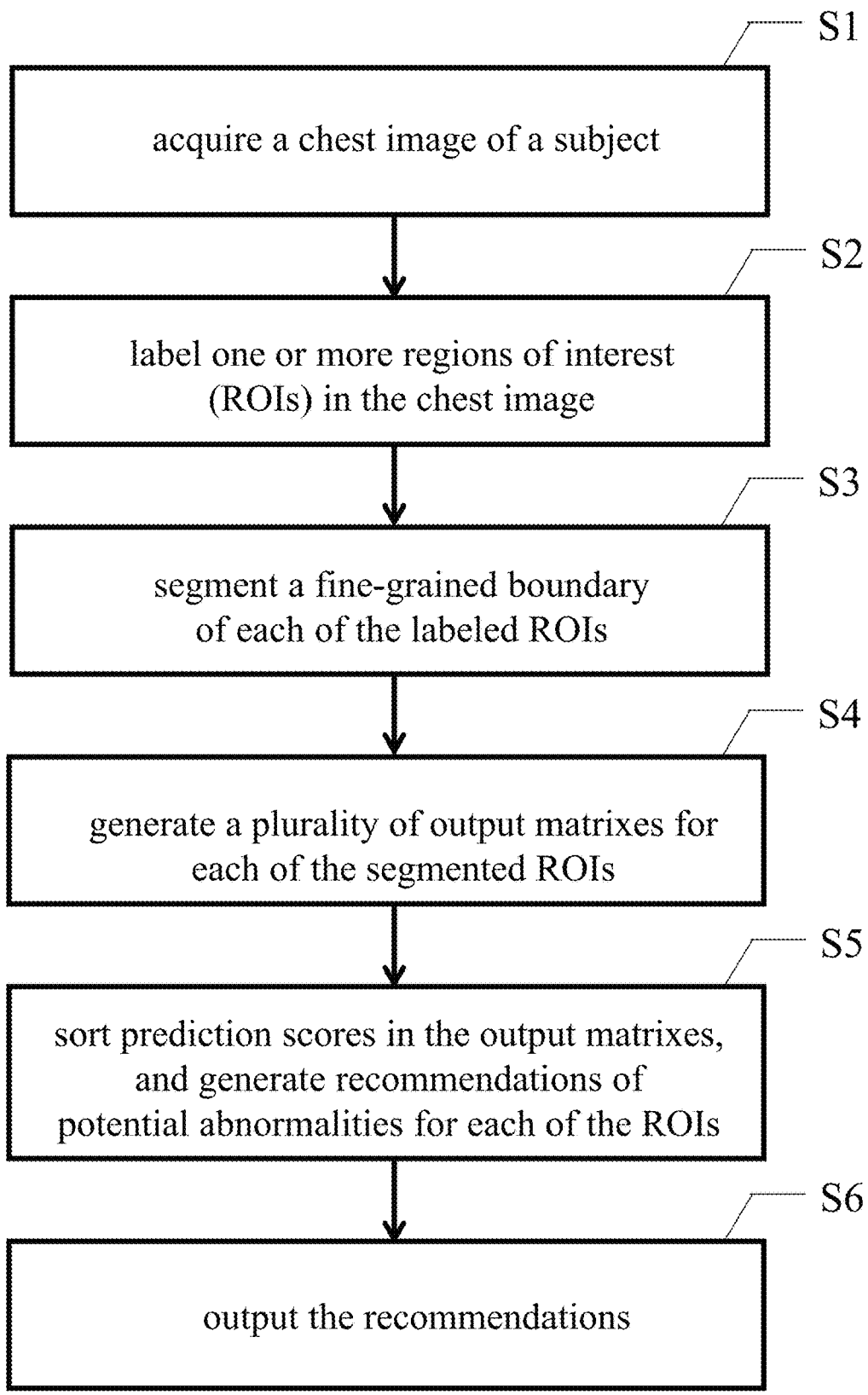
FIG. 1 shows a flow diagram of the method for detecting lung abnormalities in accordance with an embodiment of the present disclosure.

Referring to FIG. 1. An embodiment of the present disclosure provides a computer-implemented method for detecting lung abnormalities. The method includes the steps of:
- S1: acquiring a chest image of a subject;
- S2: labeling one or more regions of interest (ROIs) in the chest image;
- S3: segmenting a fine-grained boundary of each of the labeled ROIs;
- S4: generating a plurality of output matrixes for each of the segmented ROIs;
- S5: sorting a plurality of prediction scores obtained in the output matrixes, and generating a plurality of recommendations of potential abnormalities for each of the ROIs; and
- S6: outputting the recommendations.

Figure 2:
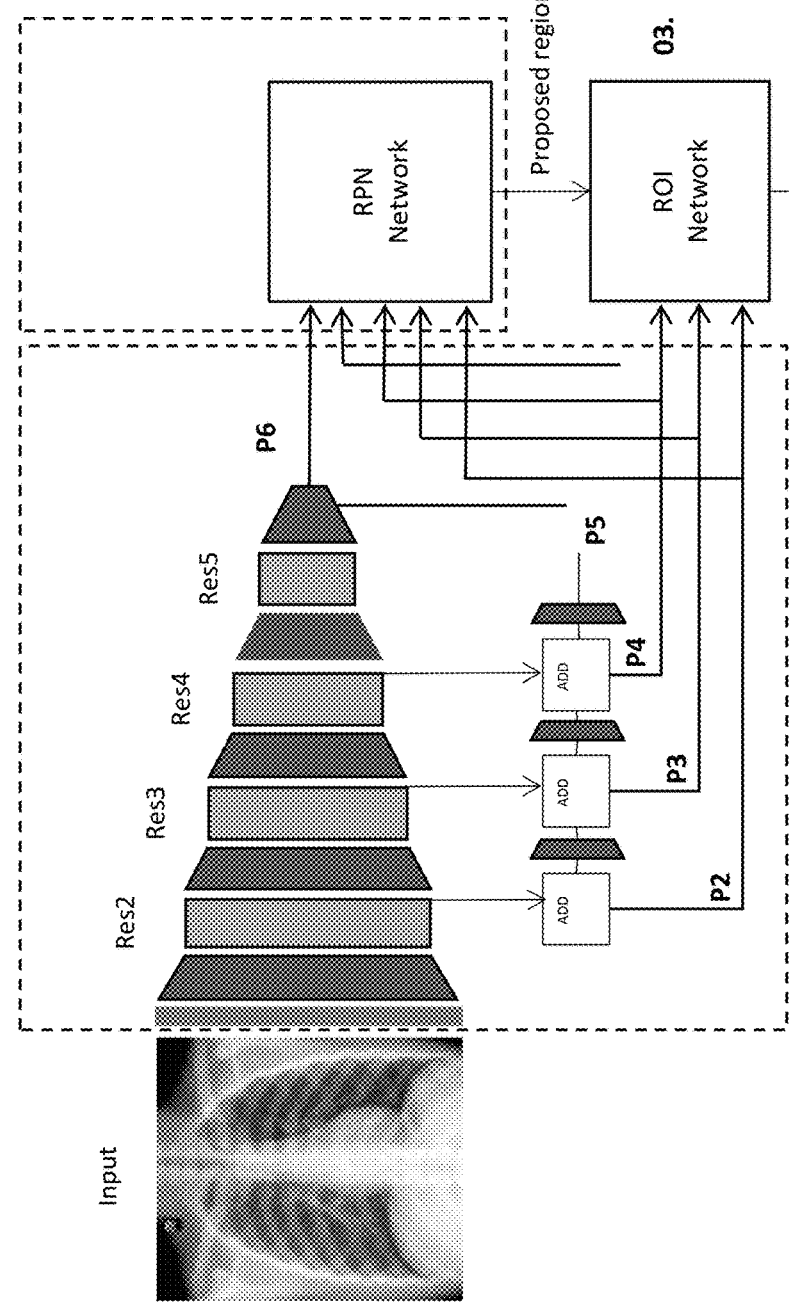
FIG. 2 shows a deep learning architecture of the SIFT system in accordance with an embodiment of the present disclosure.
Figure 3:
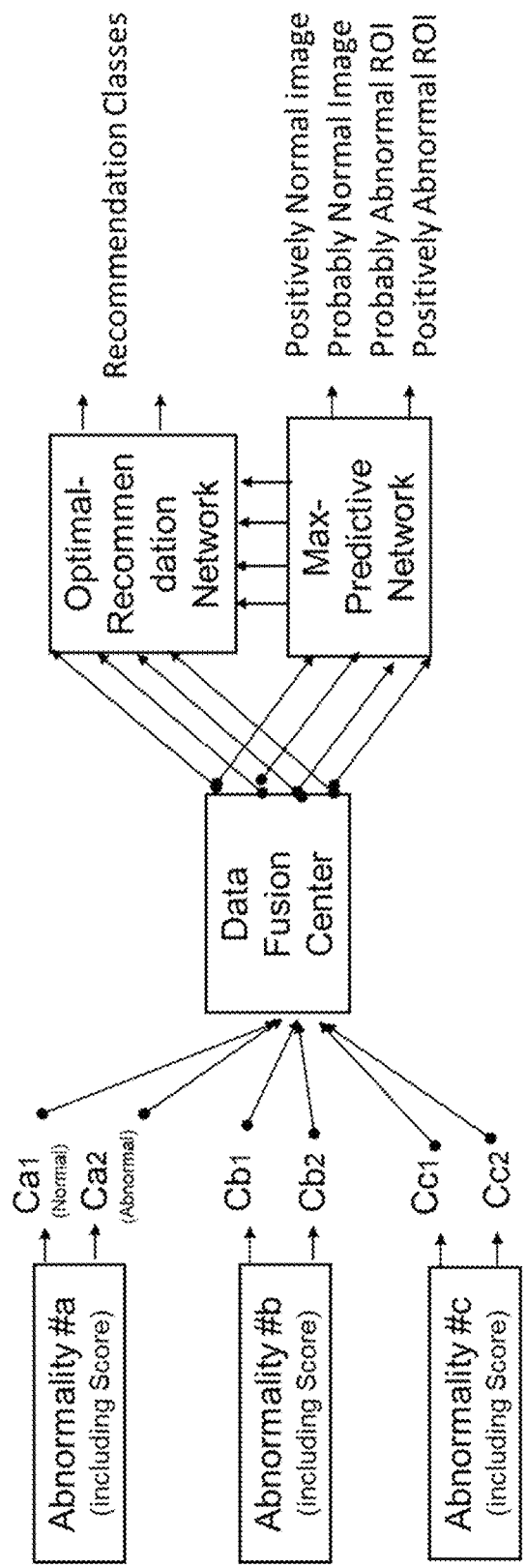
FIG. 3 shows the decision fusion network architecture in accordance with an embodiment of the present disclosure.
Figure 4:
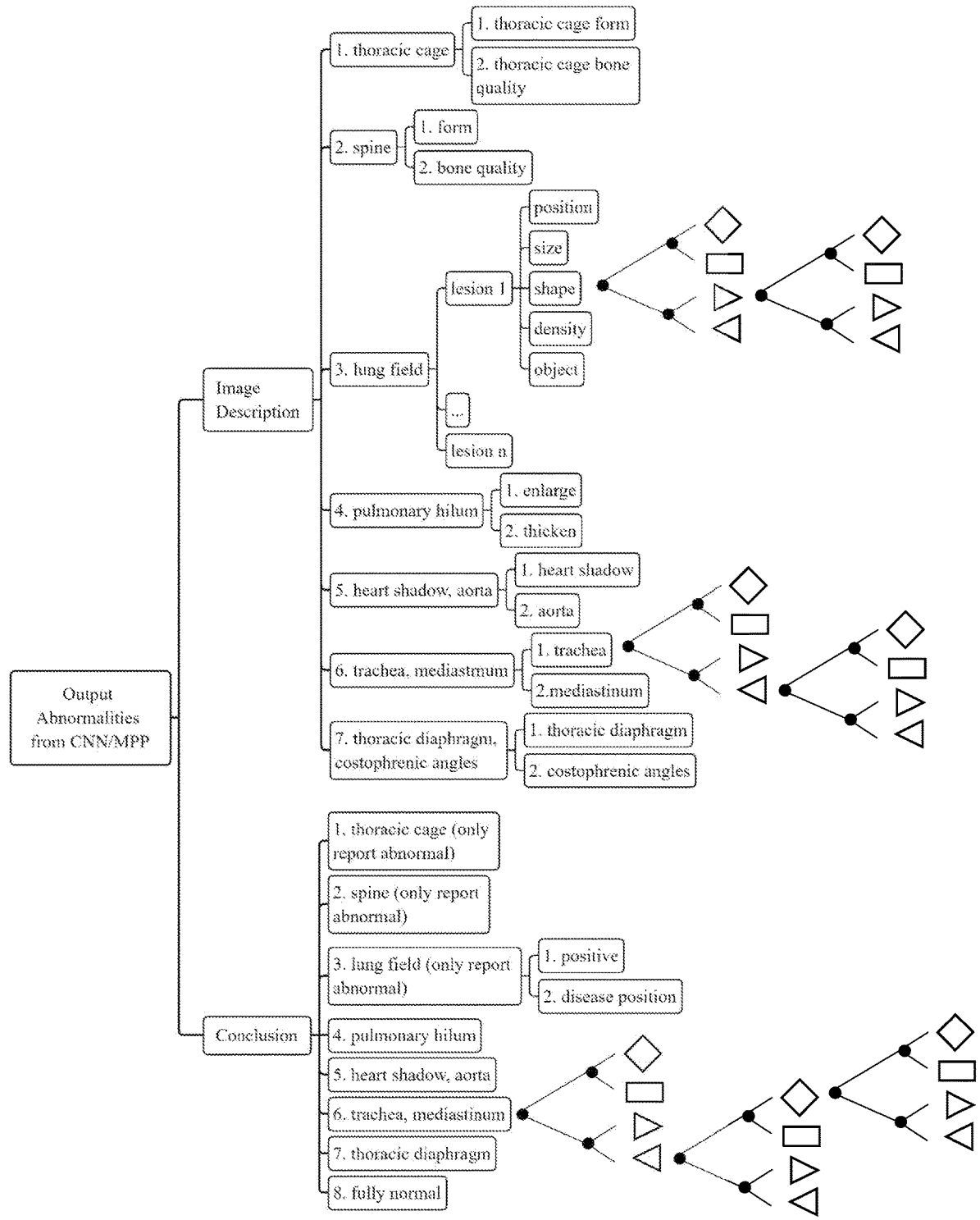
FIG. 4 shows the structure of a bifurcated gradient-boosted decision tree in accordance with an embodiment of the present disclosure.

Referring to FIG. 2 through FIG. 4. Another embodiment of the present disclosure provides a smart imagery framing and truthing (SIFT) system for detecting lung abnormalities. The SIFT system includes augmented mask regions with a convolutional neural network (Mask R-CNN) and a multilayer perceptron neural network (MLPNN) coupled to the Mask R-CNN. The SIFT system includes a top-down architecture with lateral connections developed for building high-level semantic feature maps at all scales.

As shown in FIG. 2, the Mask R-CNN includes a Feature Pyramid Network (FPN) for feature extraction, a Region Proposal Network (RPN) coupled to the FPN and for region proposals creation, and an ROI Network coupled to the FPN and the RPN and for box and mask prediction. Specifically, box prediction outputs coordinate information of boxes, whereas mask prediction describes segmentation boundaries and outputs matrixes as large as the input image.

As shown in FIG. 3. The MLPNN includes a Data Fusion Center (DFC) for fusing the matrixes outputted from the ROI Network to improve accuracy of prediction scores, a Max-Predictive Network (MPN) coupled to the DFC and for determining abnormalities having a maximum prediction score, and an Optimal Recommendation Network (ORN) coupled to the DFC and the MPN and for generating additional recommendations.

As shown in FIG. 4. The SIFT system adopts a bifurcated gradient-boosted decision tree to concatenate image descriptions and conclusions associated with the potential abnormalities and generate a sematic text report on the diagnostic results.

Referring again to FIG. 2. The FPN serves as the backbone of the Mask R-CNN combined with a pyramid architecture in which the ResNet50 network is used for the backbone network. As exemplified in FIG. 2, feature maps named P2, P3, P4, P5, and P6 are the outputs of the backbone network. Spatial resolution of the feature maps decreases from $1/4$, $1/8$, $1/16$, $1/32$ and $1/64$ in sequence.

In some embodiments, channels in Mask R-CNN may refer to the dimensions used to save features during convolution. During the feature extraction process of the Mask R-CNN, the image would be continuously compressed in the width and height dimensions, and gradually expanded in the channel dimension. General input channels refer to the size of the convolution kernel. The size of a 3×3 convolution kernel is typically 3×3×the number of input channels. Each convolution kernel (e.g., 3×3×the number of input channels) has weights parameters, and would generate a feature map of the output channel when convolution calculation is completed. Therefore, the channel outputted by the convolution calculation is the number of convolution kernels calculated by the convolution calculation of that layer, and the results of the convolution kernels may be stacked and saved in the channel dimension.

Further, the convolution calculation refers to using the convolution kernel (e.g., a small matrix) to move on the input feature map according to specified strides and order. Each movement calculates the input feature map and convolution of the current position of the convolution kernel. The sum of the products of the convolution kernel is calculated and saved in a corresponding location.

Figure 5:
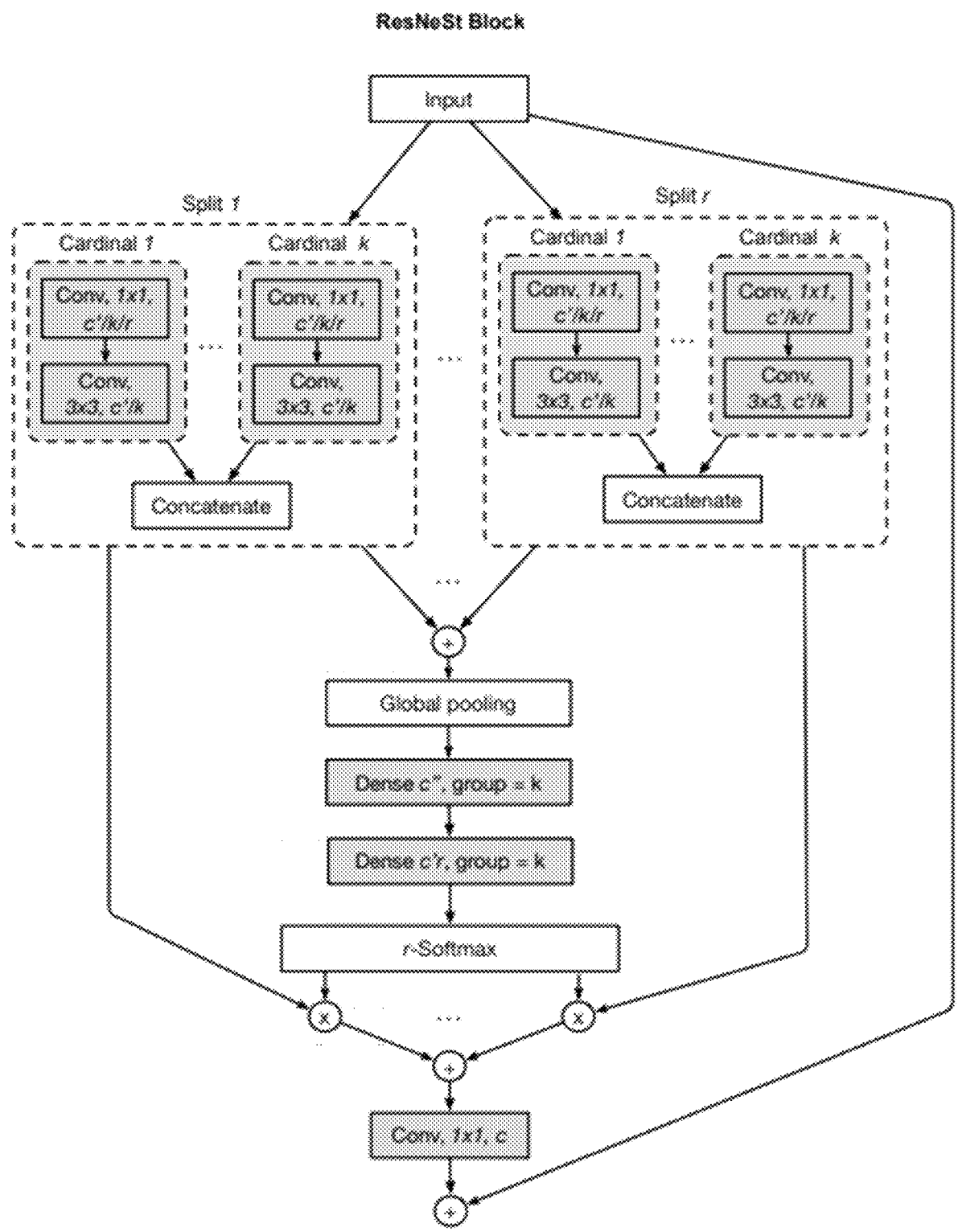
FIG. 5 shows a ResneSt network structure of the SIFT system in accordance with an embodiment of the present disclosure.

Referring to FIG. 5. In the embodiment, ResneSt replaces Resnet as the backbone for FPN. ResneSt is a Resnet-based deep neural network architecture. ResneSt introduces an attention mechanism Into the design of the network. The attention mechanism is a mechanism used to control the amount of information in the model learning process, which helps the model automatically learn key information and ignore unnecessary information.

In the attention mechanism, channel attention weights are calculated before convolution outputs. The attention weights indicate the importance of each channel, and result in weighted feature maps. The channel weights are automatically learned according to label contents by introducing model parameters, and the model introduces channel attention into the basic convolution module in the process of extracting features.

ResneSt Block uses fast convolution to extract features of input information. Fast convolution is a method that uses point convolution instead of convolution operation, thereby effectively reducing the amount of calculation of convolution operation. The ResneSt Block uses a residual connection to solve gradient disappearance in deep neural networks, and the residual connection adds the output of each layer to the input of the layer, thereby effectively reducing the loss of information in the network. The ResneSt Block also uses depth separable convolution, which can combine convolution kernels splitted into multiple smaller convolution kernels for operation and can thus reduce the number of parameters and reduce the complexity of the operation. Further, the ResneSt Block uses a convolution block with the attention mechanism, which can automatically learn what information should be paid attention to, and an attention block that uses matrix multiplication to calculate the attention weights (i.e., a probability distribution that indicates the degree of attention that should be paid to each input information position).

As illustrated in FIG. 5, the FPN splits a feature map from a channel dimension, convolves the feature map to generate a plurality of sub feature maps, concatenates and adds the generated sub feature maps, weighting the added sub feature maps to obtain a weighted feature map.

The added sub features maps may be weighted according to steps of: performing global pooling on an unweighted feature map to obtain a one-dimensional tensor containing global information; applying the one-dimensional tensor to two fully connected layers to obtain an attention tensor having a length identical to that of the one-dimensional tensor; activating a softmax function to convert the attention tensor into a probability distribution between [0, 1] by the fully connected layer; weighting the unweighted feature map according to the probability distribution; and outputting the weighted feature map.

Figure 6:
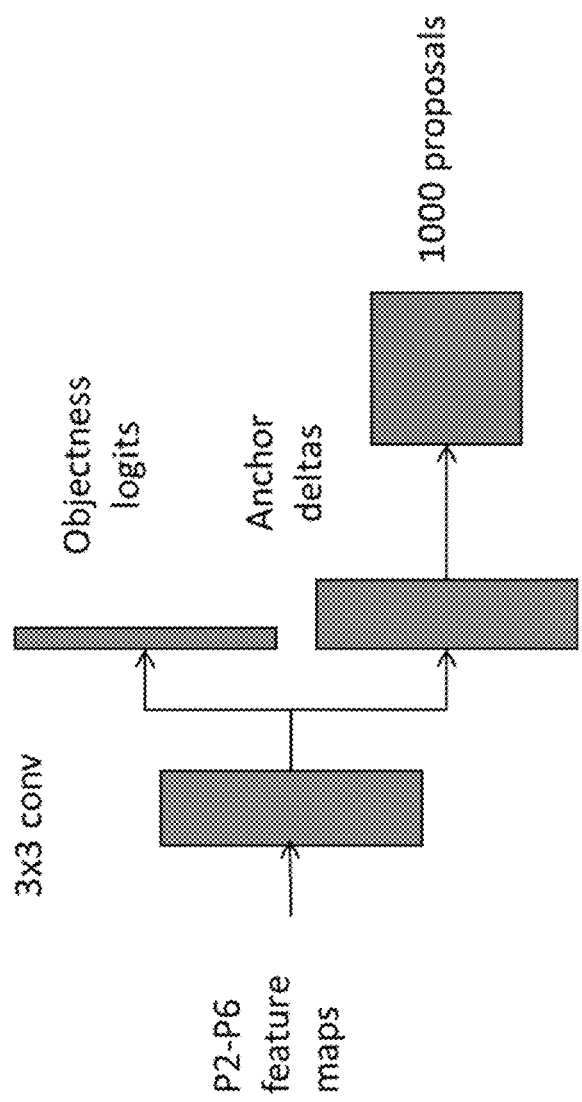
FIG. 6 shows the structure of an RPN Network of the SIFT system in accordance with an embodiment of the present disclosure.

Referring to FIG. 6. The RPN detects and segments possible ROIs with the purpose of detecting multiple objects that are identifiable within an image. The RPN also has a classifier and a regressor. For each detected or identified ROI, the RPN produces the bounding box coordinate and scores of foreground ROI.

In the embodiment, the RPN adopts a focal loss function, as represented by Equation I, for reducing class imbalance and improving prediction accuracy of difficult samples in region proposal creation. The difficult samples refer to samples that are difficult to classify or difficult to learn by the network.

$FL(pt) = -(1-pt)^\gamma \times \log(pt)$ ... (Equation 1), wherein pt is a probability of correct prediction, and $\gamma$ is a hyperparameter for controlling shapes of the focal loss function.

More specifically, focal loss is used as the classification loss of RPN and ROI Network, in replacement of the cross-entropy loss. Focal loss is a loss function used to solve the problem of class imbalance in classification. In the case of class imbalance, some classes have much more samples than others, which makes it easier for the model to predict these common classes. This can lead to lower accuracy of the model on classes having smaller sample numbers.

Focal loss solves the problem by giving larger penalties to less likely predictions. Specifically, it weights cross-entropy loss of predicted probabilities and true labels, so that the loss for samples with low predicted correct probability increases, while the loss for samples with high predicted correct probability decreases. In this way, the model pays more attention to those lesser number of categories that tends to be confusing, thus improving the prediction accuracy on these categories.

The RPN may be trained by randomly selecting a predetermined number of anchor boxes matched to each ground truth (GT) box as positive samples, thereby ensuring that samples with large ROI areas and samples with small ROI areas have equal chances to be matched as the positive samples. Positive samples may be determined according to the actual conditions.

Figure 7:
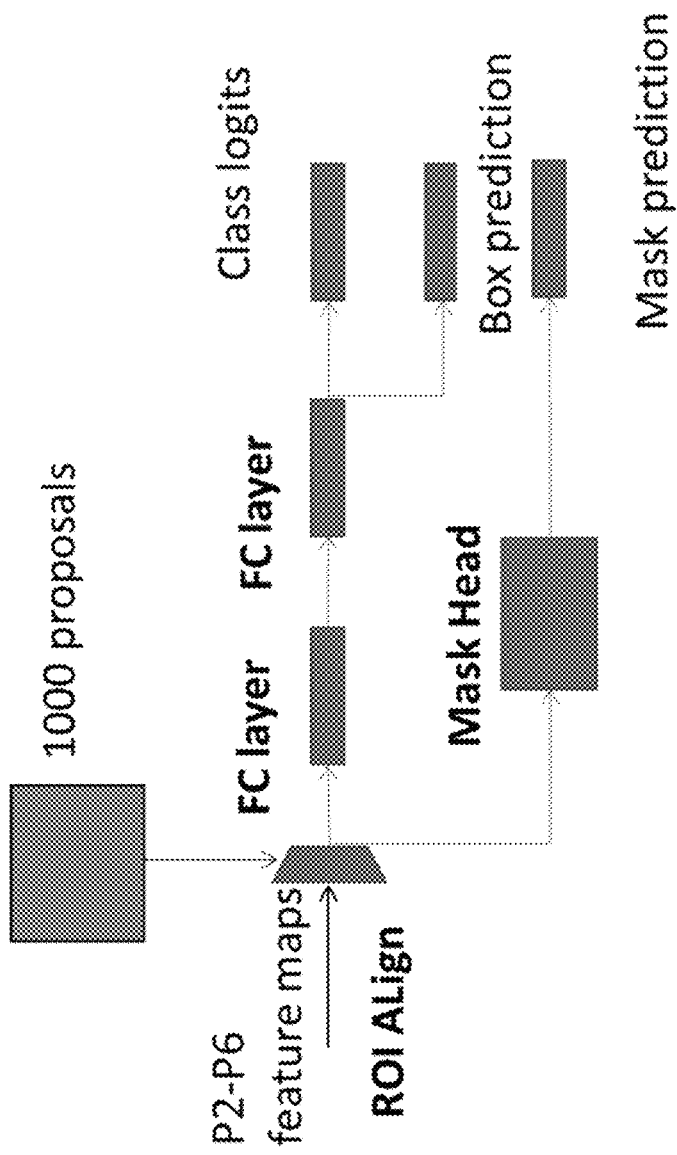
FIG. 7 shows the structure of an ROI Network of the SIFT system in accordance with an embodiment of the present disclosure.

Referring to FIG. 7. The ROI Network classifies ROIs into multiple categories of objects and obtains more accurate bounding box coordinates and segmentation results. After non-maximum suppression, about 1,000 ROIs could be sent to the ROI network.

In the embodiment, the ROI Network adopts another focal loss function, as represented by Equation II, for reducing class imbalance and improving accuracy of bounding box coordination and segmentation in box and mask prediction.

$FL(pt) = -(1-pt)^\gamma \times \log(pt) \times gtweight$ ... (Equation II), wherein pt is a probability of correct prediction, $\gamma$ is a hyperparameter for controlling shapes of the focal loss function, and gtweight is an array of weights assigned to each of the potential abnormalities.

Specifically, the parameter "gtweight" weighs diseases according to the multiple training data among the total data and increases the weight of particular diseases of interest.

Further, prediction scores may be adjusted when the result is output. Specifically, the test set may be used to determine the ROC curve for each category, and the prediction score may be adjusted according to the optimal threshold of the ROC curve, thereby preventing low-scoring categories from miss detection when the same threshold is used.

Figure 8:
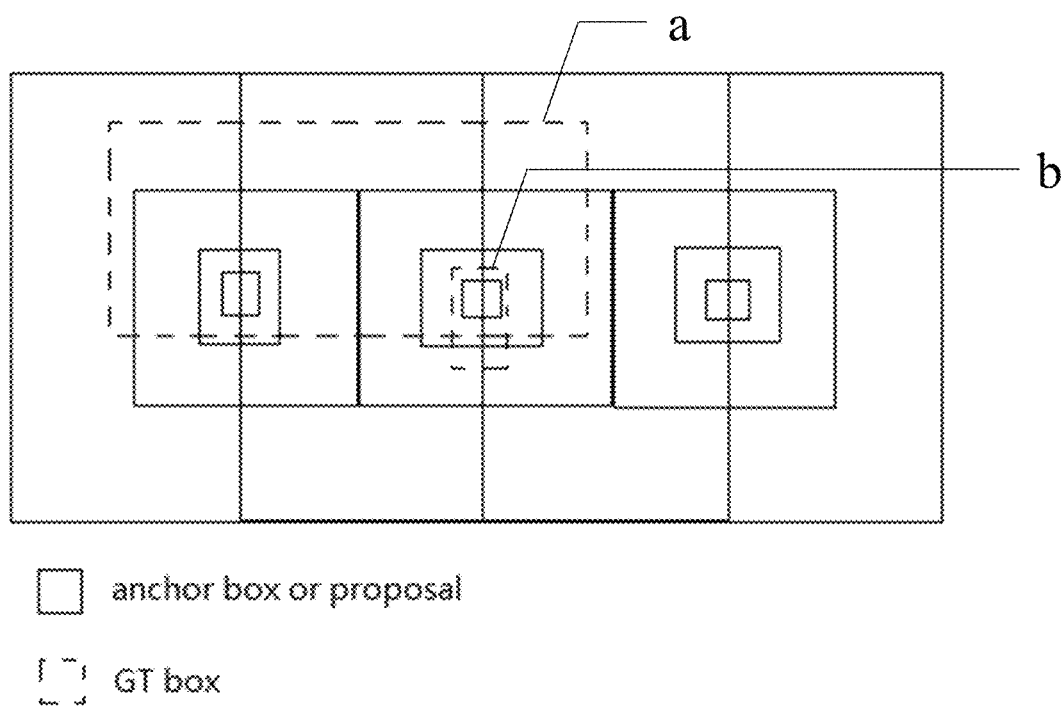
FIG. 8 shows an example of positive samples matching with large and small GT boxes.

Referring to FIG. 8. As illustrated in FIG. 8, under the same intersection over union (IOU) conditions, large GT boxes (a) may include several anchor boxes or proposals that qualify as positive samples, whereas small GT boxes (b) only include a small number of qualifying anchor boxes or proposals, therefore resulting in imbalance in positive sample matching. To avoid such imbalance problem, the ROI Network may be trained by randomly selecting a predetermined number of positive sample proposals (i.e., anchor boxes or proposals that qualify as positive samples) for each ground truth (GT) box, thereby ensuring that samples with large ROI areas and samples with small ROI areas have equal chances to be matched as positive samples. The positive sample proposals refer to more accurate anchor boxes, and may be selected under less strict non-maximum suppression (NMS) conditions (e.g., less area overlap, or an IOU threshold being less than 0.5).

Referring again to FIG. 3. The MLPNN includes a Data Fusion Center (DFC), a Max-Predictive Network (MPN) and an Optimal Recommendation Network (ORN). The MLPNN is fine-tuned with error back-propagation learning for updating weights to improve prediction accuracy.

Figure 9:
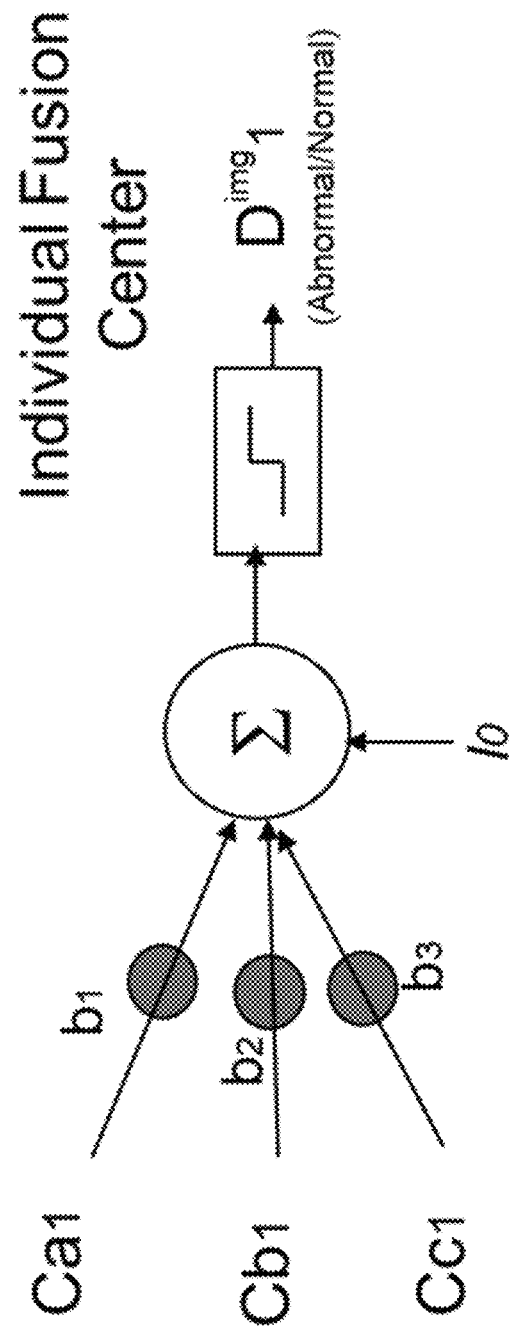
FIG. 9 shows the structure of a decision fusion center of the SIFT system in accordance with an embodiment of the present disclosure.

Also referring to FIG. 9. The DFC is a two-layer fully connected neural network. The input is the output (e.g., boxes, masks, scores, classes) of the ROI Network of the Mask R-CNN (i.e., AI prediction information of an ROI), and the output is the prediction of various diseases by the ROI Network.

Specifically, the DFC in MLPNN is a trainable network where weights of $B_{in}$ and $I_i$ are transferred from canonical form determined based on the score and performance (e.g., ROC) of each individual classification for the maximization of prediction accuracy using Bayes optimum threshold, as represented by Equation IV, for the largest likelihood ratio.

$$v_i = \Sigma_{n=1}^{N} C_{ni} B_{in} + I_i$$ (Equation IV), wherein, $v_i$ represents output characteristics; $C_{ni}$ represents input characteristics; $B_{in}$ represents weight; $I_i$ represents bias.

Meanwhile, the ROI in the same area is merged, and the score is the maximum score of the same category. Doctor's prior knowledge refers to the correlation matrix (1×66) of the disease.

Referring again to FIG. 3. MPN is a two-layer fully connected neural network. The input is the output of DFC (i.e., the scores of various diseases for each sample (or ROI)). The output is the degree of abnormality of each ROI (i.e., 4 levels according to the score: 4—determined abnormality, 3—possibly abnormal, 2—possibly normal, 1—definitely normal).

As a two-layer fully connected network, MPN takes the result of Mask R-CNN combined with prior medical knowledge extracted from medical data as input, uses feature selection technology and multivariate modeling technology to obtain initial weights, and uses doctor's labels as a supervisory signal. Backpropagation gets the model parameters.

Specifically, the MPN considers real-world prevalence of diseases and is implemented with back-propagation of error derived from the maximization of predictive value. The said real-world prevalence of diseases is measured by positive predictive value (PPV) and negative predictive value (NPV). The initial weight of MPN is calculated from PPV and NPV based upon a multivariate modeling technique along a feature selection technique to select the subset of possible abnormality giving the best PPV model.

The weight value of MPN is initialized by the combination of PPV and NPV according to the positive correlation coefficient. The combined value of the PPV and NPV may be obtained by adding and multiplying the PPV and NPV. That is, the weight value of MPN may be obtained by calculating the linear or other non-linear positive correlation function according to the above combination value.

An example of the correlation function is represented by Equation V:

$$\left.\begin{aligned} w &= f_1(P), \\ w0 + w1 + \ldots + w65 &= 1, \\ P &= f_0(PPV, NPV), \end{aligned}\right\} \quad \text{(Equation V)}$$

wherein P represents the combined value of PPV and NPV; $f_0$ represents operations such as adding and multiplying PPV and NPV; w represents a weight; and $f_1$ represents a linear or other non-linear positive correlation function for calculating the weight value.

For example, 65 lung abnormalities involved in the present disclosure, the sum of the weight value is 1.

Still referring to FIG. 3. ORN is a three-layer fully connected neural network. The input is the vector spliced by the output of DFC and MPN, and represents the possibility of each category.

In the case of abnormal MPN output, only the category with the highest score of each ROI may be focused on. The rankings generated by the MPN, DFC and ORN may be different, but the final ORN result would prevail.

The correlation matrix of the disease is obtained from the label of the labeled data. Each disease is regarded as a variable, and whether the disease occurs in each sample is used as the observed value of the variable. If occurred, it is 1; and if not occurred, it is 0. To determine the correlation coefficient of pairwise correlation of disease variables, each disease would generate a correlation coefficient with other diseases, and this correlation coefficient would be used as prior knowledge spliced into the AI results and input to MPN.

Figure 10:
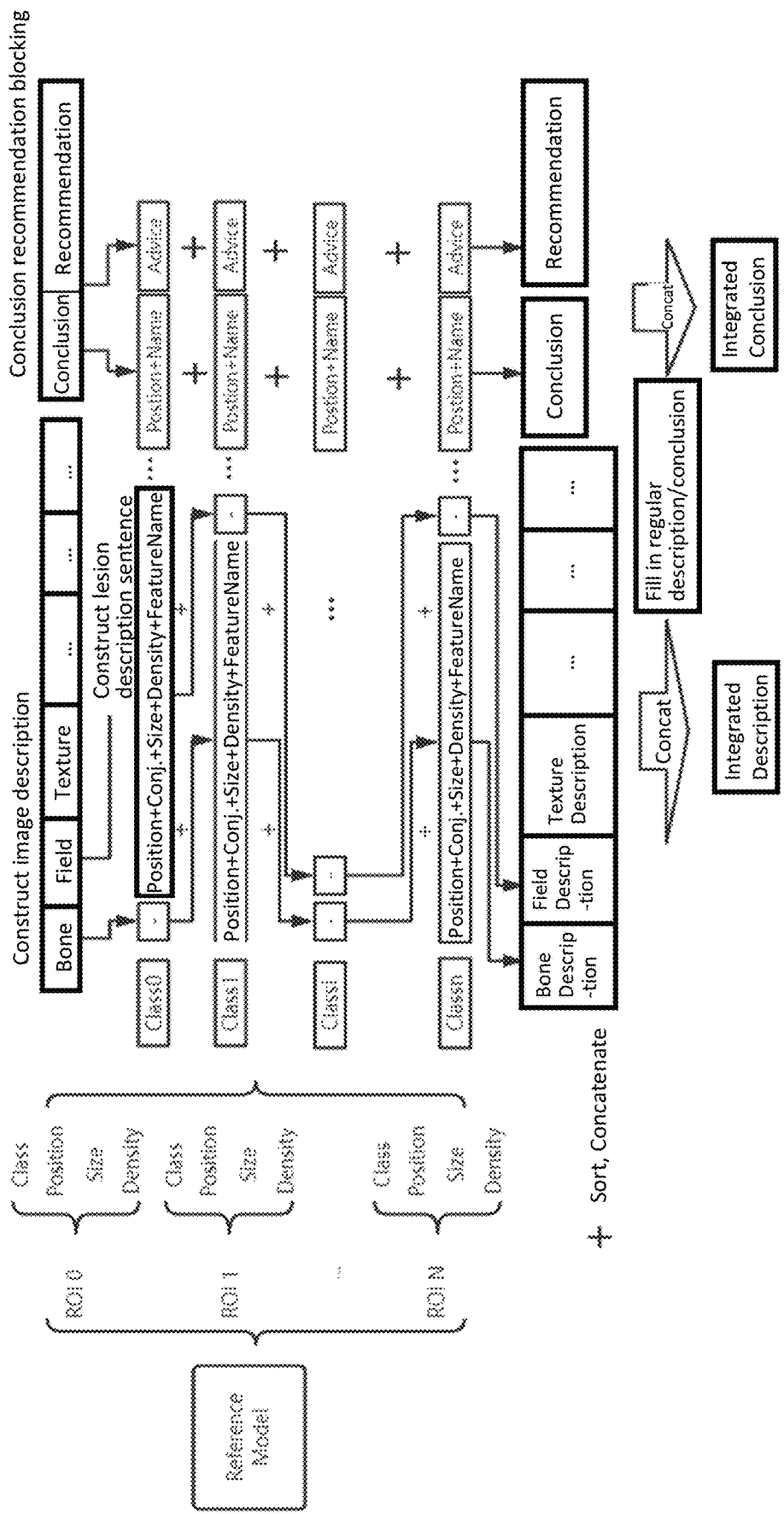
FIG. 10 shows the process of generating a knowledge tree-structured report in accordance with an embodiment of the present disclosure.

Referring to FIG. 10. The ORN is decided based on gradient-boosted decision trees. The decision tree is converted into a binary decision tree that is thus used to establish initial weight. A 3-layer MLP is implemented for a binary decision tree based on Karnaugh Map, which is a method to simplify the Boolean algebra expression. Based on probability scores generated by the integrated model on 65 different types of abnormalities, several optimal recommendations of the likelihoods of the detected and segmented positive ROI belonging to several potential abnormalities are generated.

Figure 11:
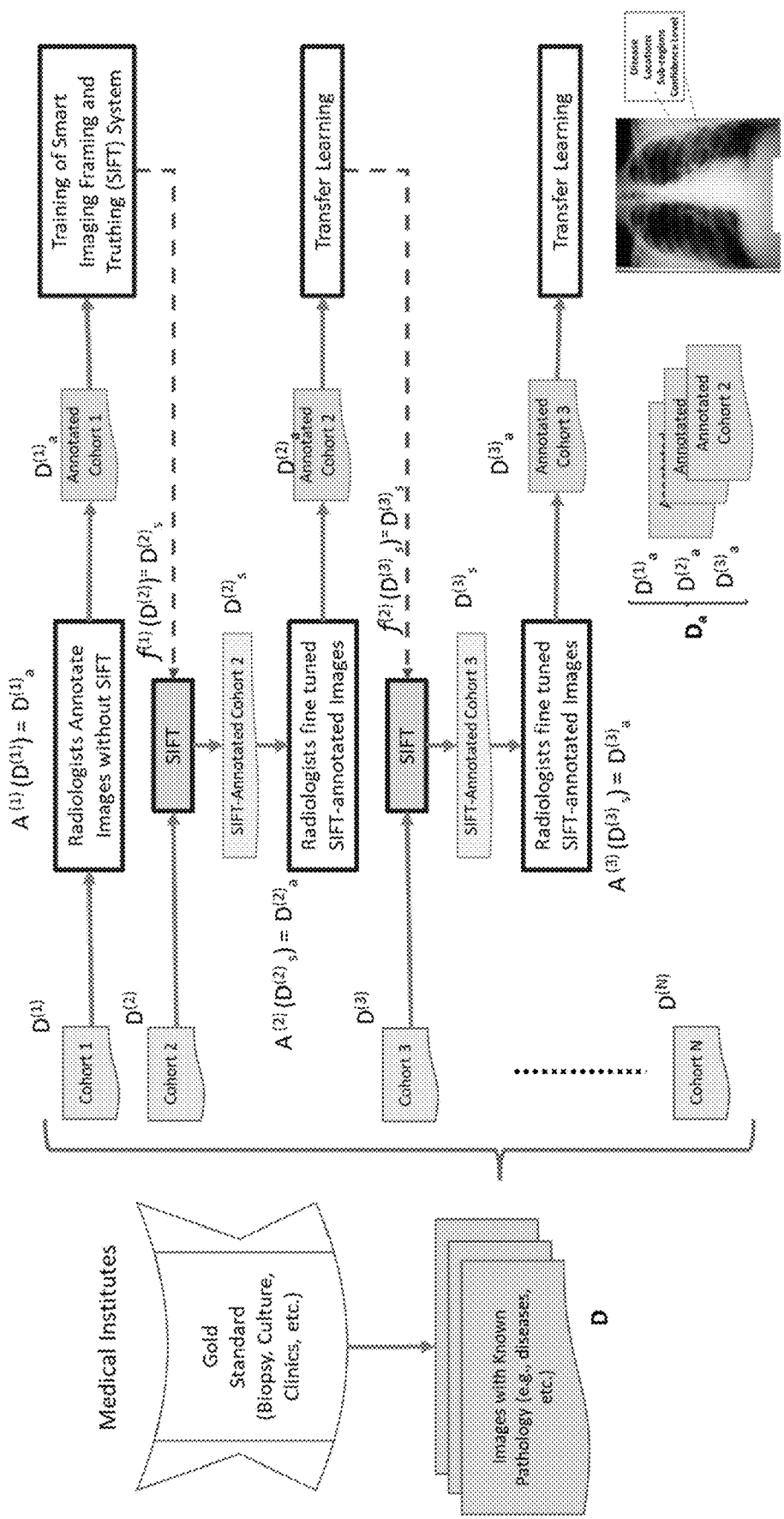
FIG. 11 shows an expert-driven fast fine-grainer annotation process implemented by the SIFT system in accordance with an embodiment of the present disclosure.

Referring to FIG. 11. In order to reduce the risk of overfitting and determine the optimal training epochs and connection weights to build above transfer learning networks, the training dataset may be divided using a ratio of 0.85 to 0.15 in all different image categories, including normal images and 65 different types of abnormalities. Note that the term "normal image" is used to indicate that there is no finding in the CXR image by radiologists. Thus, for each image category, 85% of CXR images are used to train the networks and 15% of CXR images are used to validate the network performance for different epochs and weights.

Referring again to FIG. 1. In the method implemented by the SIFT system, Step S2 may be performed in response to a user's input.

In some embodiments, the chest image may include a plurality of image layers, and Step S3 may further includes the following steps S3.1-S3.6, so as to obtain a continuous three-dimensional lesion region.

S3.1: defining the image layer having the segmented boundary as a first base layer;

S3.2: determining lesion features within the segmented boundary;

S3.3: detecting two image layers immediately adjacent to the first base layer and having the lesion features;

S3.4: segmenting regions having the lesion features in the adjacent image layers;

S3.5: defining at least one of the adjacent image layers as a second base layer; and S3.6: repeating the Steps S3.2 through S3.4 until the lesion features are no longer detected in the adjacent image layers.

For example, for a lesion found on the current layer, the prediction box of the lesion may be projected as the base to the two adjacent layers (e.g., the pair of image layers immediately above and immediately below the current layer). The following steps are performed on each of the adjacent layers: detecting and segmenting a defined area using the same model; if the lesion is detected, defining that layer as the new base and continuing detection of another pair of adjacent layers; and stop tracking upward or downward when the lesion is no longer detected in that direction.

In Step S4, the output matrix of each ROI contains at least 66 prediction scores corresponding to a potential abnormality or disease and the location of the ROI.

In the embodiment, Step S5 may include the steps of:

S5.1: fusing the output matrixes, each of which comprises the prediction scores $S_j$, each of the prediction scores is associated with one potential abnormality, wherein $0 \leq S_j \leq 1$, j=1,2, . . . , n, n is a positive integer;

S5.2: sorting the prediction scores in each of the output matrixes;

S5.3: selecting the output matrix having prediction scores greater than a prediction threshold; and S5.4: generating the recommendations of potential abnormalities according to the selected output matrix.

In some embodiments, Step S5 may further includes the steps of: when one of the ROI is overlapped by more than 30% in area by another ROI, merging the boundaries of the two ROIs; selecting, between the two ROIs, a higher prediction score associated with each potential abnormality; adjusting the selected prediction score according to Equation VI; and generating the recommendations according to the adjusted prediction score, $$S = \begin{cases} \dfrac{\text{score}}{T} * 0.5 & \text{score} \leq T \\ \dfrac{\text{score} - T}{T} * 0.5 + 0.5 & \text{score} > T \end{cases}, \quad \text{(Equation VI)}$$

wherein T represents an optimal threshold.

The optimal threshold T may be obtained by determining the ROC index for each disease type in the test set and obtaining the optimal threshold T of the ROC index (i.e., the score of a point in the ROC curve closest to (0,1)), or by using Bayesian optimal threshold technique, which defines the cost of wrong classification in each class and traverses the threshold to minimize the Bayesian risk to obtain the optimal threshold, to obtain the optimal threshold T of each class.

Regarding the thresholds of four abnormal levels (i.e., 4—determined abnormality, 3—possibly abnormal, 2—possibly normal, 1—definitely normal), score adjustment is performed during outputting scores by the Max-Predictive Network (MPN). After threshold adjustment, 0.5 may be used to distinguish positive from negative. The score at which negative predictive value (NPV)=99.5% in the negative predictive value-total predictive normal (NPV-TPN) curve may be used as threshold T1 for determining negative, and the score at which positive predictive value (PPV)= 99.5% in the positive predictive value-total predictive positive (PPV-TPP) curve was used as threshold T2 for determining positive. In other words, score<T1 may be determined as definitely negative, T1<score<0.5 may be determined as possibly negative, 0.5<score<T2 may be determined as possibly positive, and score>T2 may be determined as definitely positive.

Regarding the generation of recommendations, the diseases ranked top 6 in output scores by the ORN may be provided as recommendations. However, only those exceeding the minimum threshold of 0.001 would be recommended. When the MPN determines a sample to be positive, only the disease having the highest score may be recommended.

In some embodiments, the method may further include the steps of: receiving a user's selection of one or more of the generated recommendations; and concatenating semantic expressions associated with the selected recommendations to generate a diagnostic report.

In some embodiments, the method may further include the steps of: constructing a knowledge tree module associated with image features of various lung abnormalities; obtaining image descriptions and conclusions of each of the ROIs; and concatenating the image descriptions and conclusions according to the knowledge tree module.

By using the SIFT system of the embodiment of the present disclosure, the class, size, density, position, and other characteristics of prediction results can be obtained, and the image description and conclusion of each class can be obtained by artificially constructing a knowledge tree-structured module suitable for various diseases/signs, and then the image descriptions and conclusions of each class may be spliced in sentences according to modules.

Referring again to FIG. 4. According to the embodiments of the present disclosure, each detected ROI corresponds to one or more of features, including class (e.g., disease type), size, density, and position, and each class may correspond to the size, density, and position of multiple ROIs and other features. The model describes various categories, such as bone quality, lung field, texture, hilum, cardiovascular, pleural angle, tracheomediastinum, etc., and constructs lesions of each class in each category according to the characteristics, such as size, density, and position obtained in advance. The description sentences may be sorted and spliced according to the actual lesions, and the description sentences of each class may be spliced to obtain the corresponding descriptions, such as bone description, lung field description, texture description, lung hilar description, cardiovascular description, pleural angle description, and tracheomediastinal description. An integrated description of the CXR image may be obtained after re-splicing.

The format of each ROI description sentence may be: position+conjunction+size+density+feature name. In each class, different lesion description sentences correspond to pre-set conclusions and recommendations. The conclusions include position+name, and the conclusions and recommendations of each class are spliced to obtain an integrated conclusion. Further, in blank parts not involved in the pre-set descriptions and conclusions, regular descriptions and conclusions are filled in.

The report generation method of the embodiment of the present disclosure can quickly and automatically match disease names and generate corresponding strings to generate reports and descriptions.

Further, when interpreting the CXR image, the SIFT system may allow radiologists to manually delete lesions and/or label additional lesions in the image. That is, the SIFT system may allow dynamic modification of the output results, and generate corresponding text descriptions and conclusions in real time.

In some embodiments, the possibility of each abnormality may already present in the output score of Mask R-CNN. The subsequent DFC-MPN-ORN may only be the output of score adjustment and an increase in abnormality levels.

In some embodiments, training is performed by using image enhancement or data augmentation approaches, such as flipping, rotating, cropping, random color change, reverse color, noise, image quality reduction, to improve robustness of the model of the SIFT system. Additionally, for rare samples, the penalty weight of classification is increased. Complex and diverse data enhancement schemes are used on the data, and independent thresholds are set relative to the same threshold to ensure that the classification performance on small-sample diseases would not be affected by other diseases. Therefore, the embodiments of the present disclosure also exhibit strong robustness on disease types having small data sample sizes.

Figure 12:
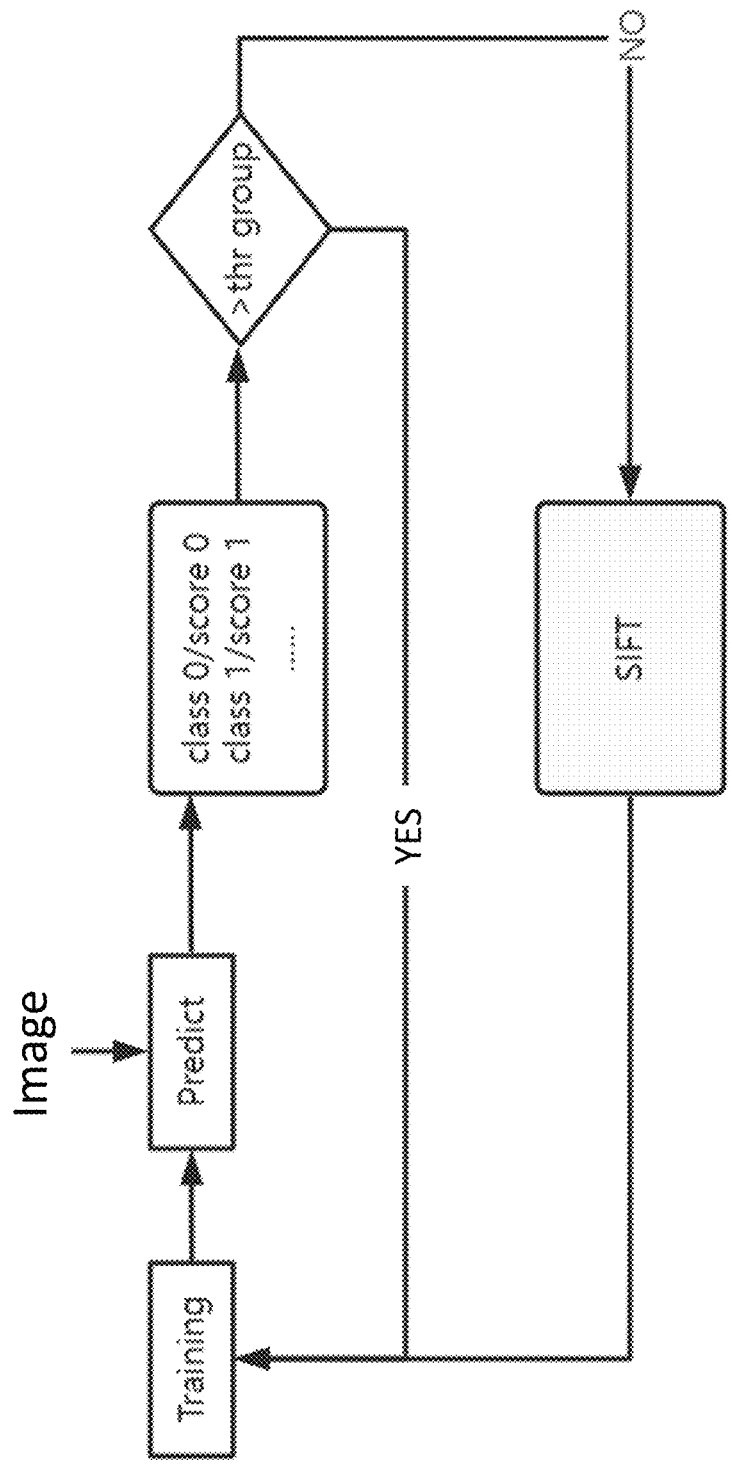
FIG. 12 shows a flow chart of a training approach for the SIFT system in accordance with an embodiment of the present disclosure.

Referring to FIG. 12. The SIFT system is trained according to the steps of: determining the prediction score of an input image; and if the prediction score is greater than current accuracy of the Mask R-CNN, including the input image into training dataset of the SIFT system, or if the prediction score is smaller than the current accuracy of the Mask R-CNN, re-training the SIFT system using the input image with correct annotations.

Specifically, after the model of the SIFT system is trained with existing dataset, an image is inputted to the model for prediction. After the classification and prediction score of the image are determined, the prediction score is compared with a threshold value, which reflects the current accuracy of the model (or the Mask R-CNN). If the prediction score is greater than the threshold, the image would be included into the training dataset. Alternatively, if the prediction score is smaller than the current accuracy of the model, annotations of the image would be corrected manually, and the image having correct annotations would be inputted into the SIFT system for retraining.

The training approach efficiently and effectively enables the SIFT system to annotate millions pieces of case data with high accuracy. Over 70% of the annotations need not be corrected or modified manually.

Figure 13:
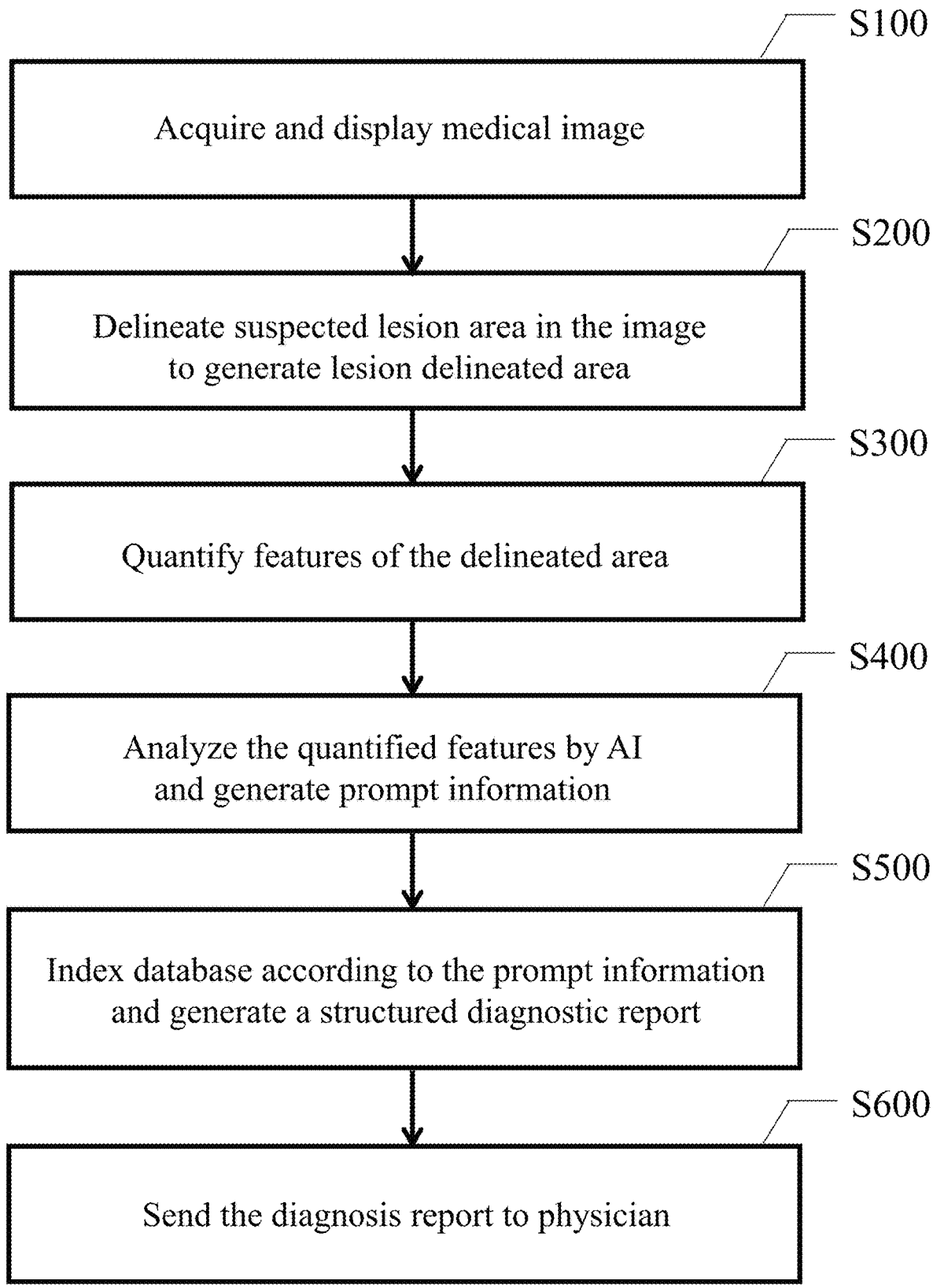
FIG. 13 shows a flow diagram of a medical image-based diagnostic report generation method in accordance with an embodiment of the present disclosure.

Referring to FIG. 13. Yet another embodiment of the present disclosure provides a medical image-based diagnostic report generation method. As shown in FIG. 13, the method includes the following steps S100-S600:

S100: acquiring and displaying a medical image of a subject;

S200: delineating a suspected lesion area in the medical image to generate a lesion-delineated area;

S300: quantifying features of the lesion delineated area;

S400: analyzing the quantified features by AI technology and generating prompt information;

S500: indexing a pre-set expert index database according to the prompt information and generating a structured diagnostic report; and S600: sending the diagnostic report to a physician for the physician to complete drafting of the diagnostic report.

The method according to the embodiment improves the efficiency of physicians (or radiologists) in reading medical images and preparing diagnostic reports, enables inter-regional communication between hospitals, and advances the standardization, structuring, and electronization of diagnostic imaging reports.

In the embodiments, the medical image may be X-ray chest radiographs. The physician uploads the subject's chest image in DICOM format to a server via a browser. The back-end receives the image. After uploading, the physician can quickly view the uploaded chest image in the list of uploaded images. The uploaded chest image can be displayed in full in the browser, enabling the adjustment of the content of the displayed medical image.

When reviewing the chest image, at least one suspected lesion area is delineated, thereby generating a lesion-delineated area. After the lesion area and lesion type are obtained, a system implementing the method quantifies features of the delineated area according to the selected lesion type. The features may include density, horizontal and vertical diameters, roundness, burr, etc. Meanwhile, a report is generated with corresponding conclusions and recommendations, which are prepared by medical professionals and saved into the database. Once the report is generated, the physician can review the report, correct any inaccuracies, and save the report.

According to the embodiment, the method can improve the efficiency of chest film reading, semi-automatically and automatically target suspicious lesions, quantify lesion features, promptly generate structured reports based on lesion categories and features, index expert database based on lesion features, and self-updates expert report database.

Further, the step S200 of delineating a suspected lesion area in the medical image to generate a lesion delineated area may include the following steps: acquiring physician's instructions of a suspected lesion area; and performing close-loop delineation on the suspected lesion area according to the physician's instructions.

Specifically, the delineated suspected lesion area provides a target location for subsequent quantitative analysis of the lesion.

Further, step S200 may include: acquiring a click command from the physician on a target area in the medical image; and delineating the target area to generate the lesion delineated area. Prior knowledge of the consistency of density features in surrounding areas may be used to generate the delineated area.

In practice, the target area may be depicted by dragging the mouse or touching the tablet. For lesion areas with concentrated features, after the lesion location is indicated by touching, automatic delineation of the indicated location is performed, thereby reducing the tediousness of manual delineation. The delineation is based on the prior knowledge that the density of the indicated area is consistent with the density of the surrounding areas.

Further, step S200 may include: obtaining a pre-trained AI model for identifying multiple diseases; inputting a medical image into the AI model; and generating lesion-delineated areas based on the input.

In practice, a fully automated AI-based recognition model pre-trained with multi-disease recognition capability may be introduced to predict multiple diseases on the received image. The results may be displayed directly to doctor's review systems. The AI-based multi-disease recognition system can analyze images without manual sketching and touching, and can annotate suspected lesions on the images with different color grades to indicate different confidence levels for reference and modification by the physicians.

Further, when the medical image is a multilayer image, the step S600 of sending the diagnostic report to a physician may further include: analyzing the lesion delineated area on a single annotated layer based on the continuity of layers and lesion features in the medical images; and delineated similar lesion areas by automatically tracking n consecutive layers above and below the annotated layer, wherein n is a positive integer.

For computer tomography (CT) and magnetic resonance (MR) imaging modalities consisting of multiple image layers, in addition to basic functions of a single layer, an upper and lower layer tracking function may be added to multilayer labeled areas. In other words, by analyzing the area delineated on a single layer based on continuity of layers and lesion features in the CT and MR images, the upper and lower n layers of the labeled layer are automatically tracked, and similar lesion areas are delineated and displayed, thereby reducing the tediousness of manual processing and improving efficiency.

The specific process is as follows: firstly, based on the prior knowledge that the last layer has continuity and similarity, the labeled area is shifted to the adjacent upper and lower layers. At this point, the target area slightly deviates from the initial tracking area. Next, the selected area is extended or contracted according to pixel area consistency. The above steps are repeated in the most optimal way until the pixel area consistency is below the optimal threshold, which means the semi-automatic annotation is completed. The process is repeated until the pixel area consistency is below the set optimal threshold and the annotation of the entire CT or MR image is completed.

The method of the embodiments of the present disclosure is not limited and is applicable to other imaging techniques, such as digital radiography (DR). The content of the diagnostic report is not limited to a certain disease of a certain tissue.

Figure 14:
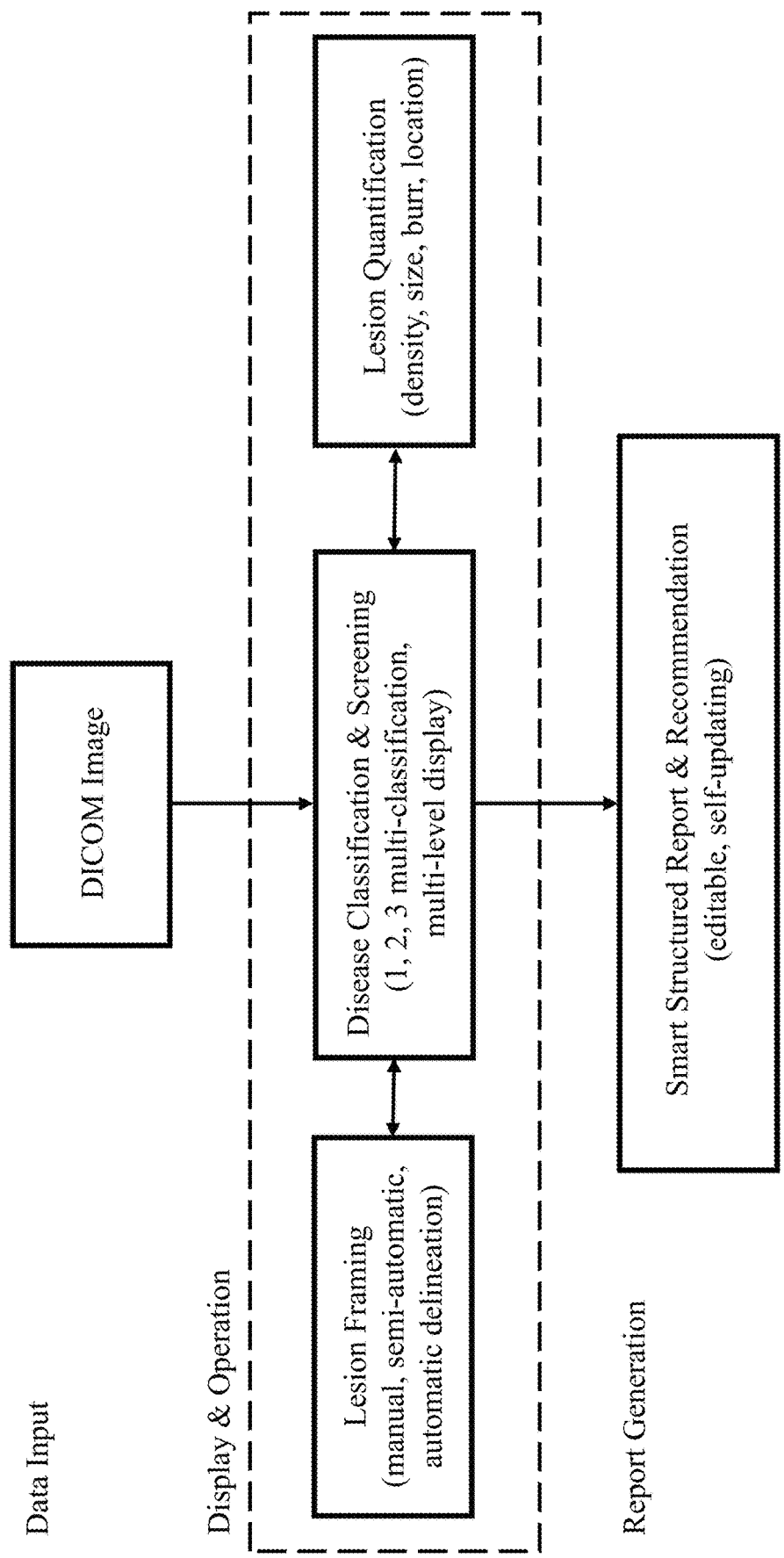
FIG. 14 shows a flow diagram of another medical image-based diagnostic report generation method in accordance with an embodiment of the present disclosure.

Referring to FIG. 14. An embodiment of the present disclosure provides an application of the medical image-based diagnostic report generation method. The method includes the following steps:

Data input: The input data is mainly in DICOM or other mainstream data formats for medical imaging, and is for viewing and subject to subsequent operations.

Display and operation: Mainly, lesion area framing, lesion classification and screening, and lesion quantification are included. Specifically, the lesion area may be framed manually, semi-automatically, and/or automatically. The lesions may be highlighted and graded for easy selection of multiple diseases. The contents for lesion quantification may include density, size (i.e., vertical and horizontal diameters), burr, and location. Lesion quantification is critical in that it provides the data basis for intelligent report recommendations.

Report Generation: The expert database is indexed to generate a structured report containing conclusions and recommendations, which are sent to hospital diagnostic systems for physicians to complete drafting of the diagnostic report. The report is editable and the system library of generated reports is capable of self-updating.

Figure 15:
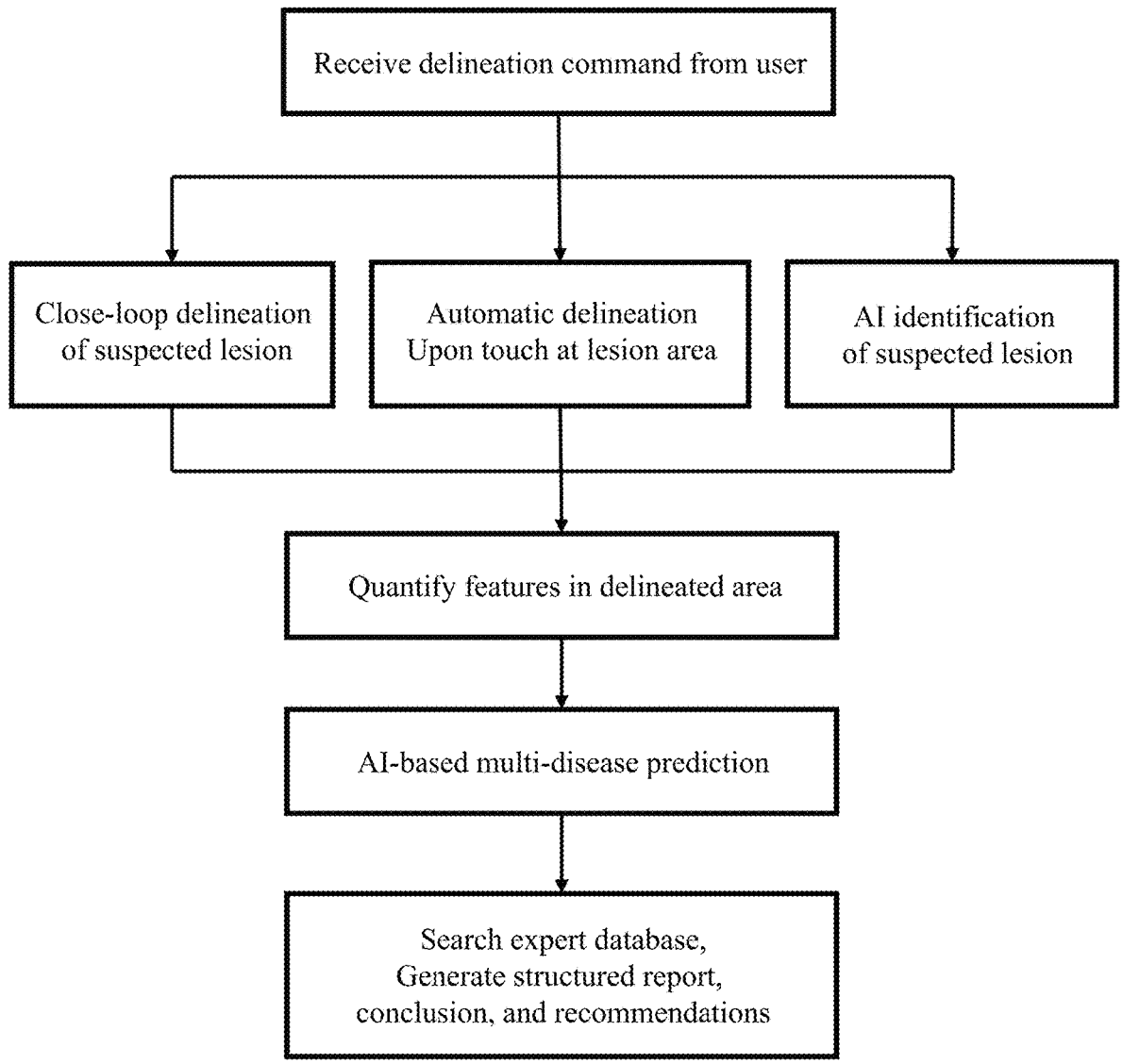
FIG. 15 shows a flow diagram of display and operation of the medical image-based diagnostic report generation method in accordance with an embodiment of the present disclosure.

Referring to FIG. 15. Operation and display of the medical image-based diagnostic report generation method may include the following steps.

After a delineation command is received from a user, suspected lesion areas are delineated by close-loop delineation, semi-automatic delineation, and AI-based fully automatic identification.

Specifically, in semi-automatic delineation: after a lesion area is indicated by touching, delineation of the indication area is automatically performed according to prior knowledge of consistency between density of the indicated area and density of the surrounding area. The image is processed mainly by extension of the indicated area based on pixel area consistency, and by repeating the above steps until the pixel area consistency is lower than the set threshold. Accordingly, the semi-automatic annotation is completed.

In AI-based fully automatic identification: AI models pre-trained with multi-disease recognition capability may be used to predict multiple diseases on the received images and to display the prediction results directly to physicians' review systems. The AI-based multi-disease recognition system can analyze and annotate suspected lesions on the image by different color grades to indicate different confidence levels for physicians' reference and modification.

AI models for AI-based automatic identification of lesion areas are not limited to recognition of a particular disease in a particular tissue/organ. The recognition algorithm used may be either a traditional image algorithm or an AI algorithm. The main purpose is to provide an inventive method for acquiring data sources that provide quantitative metrics for diagnostic imaging reports.

As shown in FIG. 15, once the lesion area and lesion type are obtained in the three above-mentioned approaches, a three-tiered (or multi-tiered) list of diseases would be automatically popped up in the vicinity for physicians to select. The three-staged list of diseases is sorted according to the degree of suspicion. Based on the selected disease, the features of the delineated lesion area (e.g., density, vertical and horizontal diameters, roundness, burr, etc.) would be quantified. Meanwhile, a report showing corresponding conclusions and recommendations would be generated.

Further, AI multi-disease analysis may be performed for identification of suspected diseases in the annotated areas, thereby providing optimal disease alert messages. Radiologists may move, delete, or add to update the above-mentioned contents. The expert database is indexed to generate a structured report containing conclusions and recommendations, which is sent to hospital diagnostic systems for radiologists to complete drafting of the diagnostic report.

Figure 16:
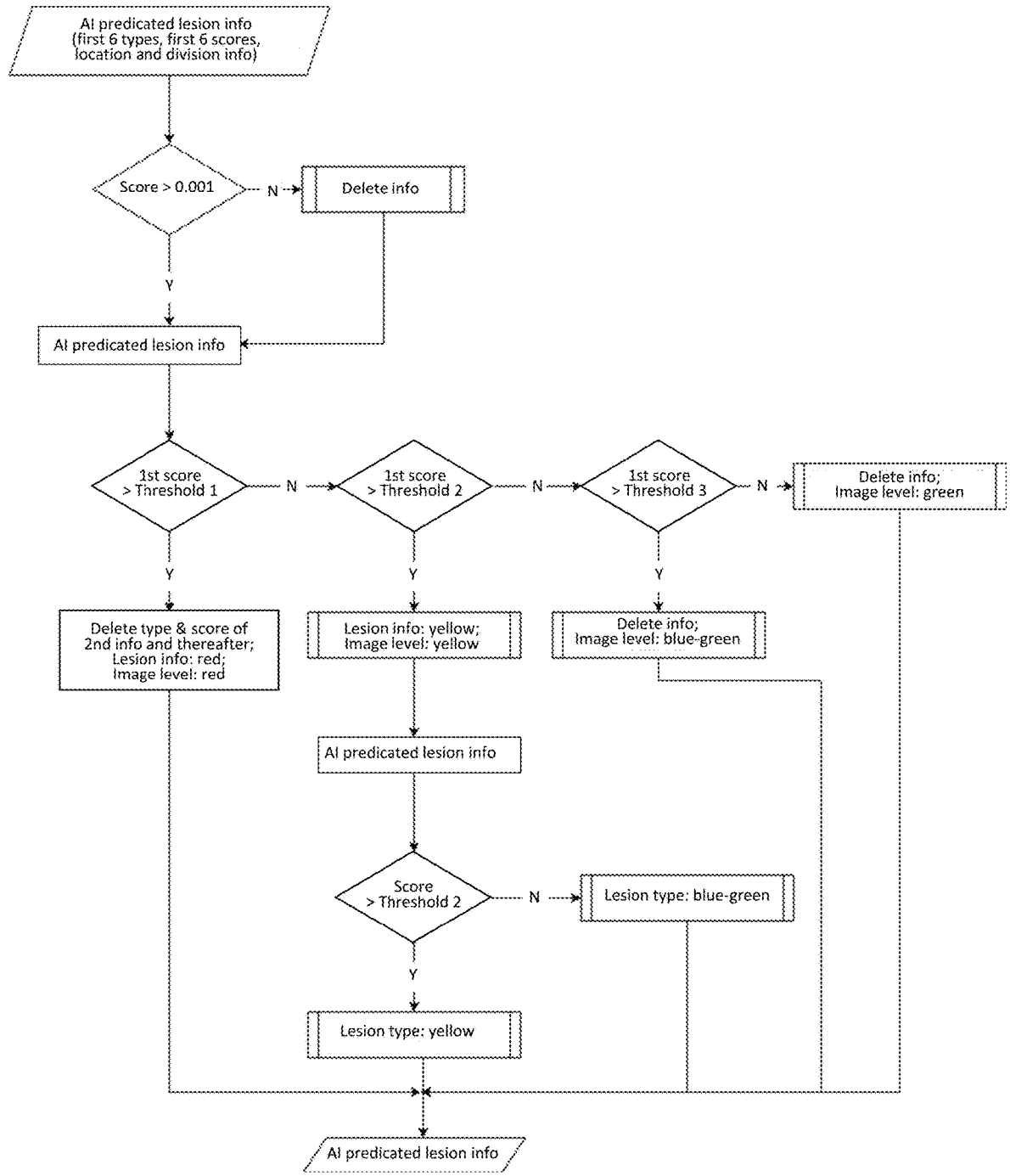
FIG. 16 shows a flow diagram of a multi-disease classification and grading process of the medical image-based diagnostic report generation method in accordance with an embodiment of the present disclosure.

Referring to FIG. 16. A multi-disease classification and grading process of the medical image-based diagnostic report generation method may include the following steps:

First, the AI model makes lesion prediction on the input image, and takes the first 6 prediction targets, including category, location, and score. Target information having scores greater than the cutoff threshold of 0.001 would be retained, while others would be deleted.

Thereafter, if the confidence level of the target having the highest confidence score is greater than Threshold 1, the second and subsequent categories and scores would be deleted. Lesion information may be set to red and image level information may also be set to red.

If the confidence score of the target having the highest confidence score is less than or equal to Threshold 1 and greater than Threshold 2, the lesion information may be set to yellow and the image level information may also be set to yellow. Alternatively, if the remaining targets are greater than Threshold 2, they may also be set to yellow; otherwise, they may be set to blue-green.

If the confidence level of the target having the highest confidence score is less than or equal to Threshold 2 and greater than Threshold 3, the lesion information would be deleted and the image level information may be set to blue-green. Alternatively, if the confidence level of that target does not meet the above-mentioned requirement, the lesion information would be deleted and the image level information may be set to green.

Accordingly, the AI prediction results would be presented in 3 levels of confidence based on the above screening criteria, thereby facilitating physicians' operations.

In FIG. 16, Threshold 1 represents the score at which the positive predictive value (PPV) is 95%. Threshold 2 represents the score at which Euclidean distance at the upper left corner is the shortest in the ROC curve. Threshold 3 represents the score at which the negative predictive value (NPV) is 99%. PPV is the number of correct positive images over the number of predicted positive images×100%. NPV is the number of correct negative images over the number of predicted negative images×100%.

Figure 17:
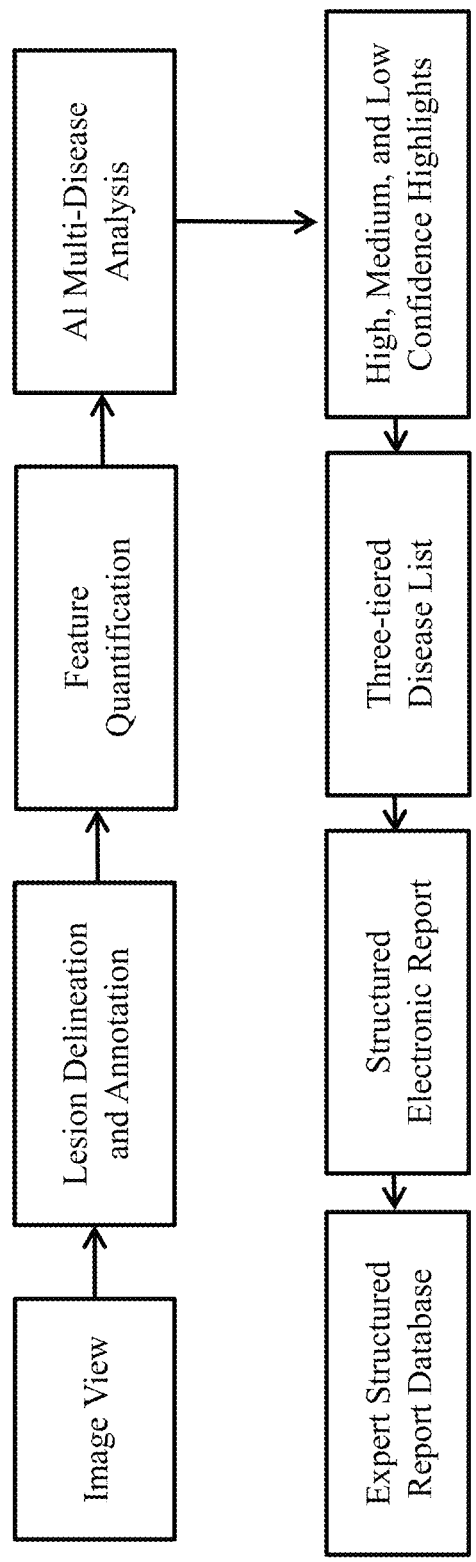
FIG. 17 shows a schematic diagram of functional modules of the medical image-based diagnostic report generation method in accordance with an embodiment of the present disclosure.

Referring to FIG. 17. The embodiments of the present disclosure possess several functions, including image view, lesion delineation and annotation, feature quantification, AI multi-disease analysis, confidence highlight, disease list, structured report, and expert database.

Specifically, the image view function allows acquiring, displaying and manipulating images, and mainly involves medical DICOM data protocols. The lesion delineation and annotation function highlights suspected lesion areas, and includes manual delineation, semi-automatic delineation, and fully automatic AI-based lesion identification. The lesion quantification function quantifies the selected lesion areas. The AI multi-disease analysis function predicts suspected diseases in the target lesion area and gives recommendations for the most suspected diseases.

The high, medium, and low confidence highlight function provides highlighted messages in a hierarchical manner for predicted diseases based on a combination of test data and clinical data. The three-tiered disease list presents a list of diseases in three tiers based on AI prediction results, and is provided to physicians for further confirmation to facilitate diagnosis and improve selection efficiency. The structured electronic report function combines the results from feature quantification, AI multi-disease analysis, and confidence highlights, and a three-tiered disease list, and indexes the expert report database to match the best-structured report. The structured expert report database is an update of the initial expert report database and is self-iterating thereby improving the quality and accuracy of expert reports.

From the above-mentioned embodiments, the methods of the present disclosure provide convenience for physicians in reviewing medical images, reduce the time spent by radiologists in quantitative analysis of lesions and preparation of diagnostic reports, and promote standardization, structuring, and electronization of diagnostic reports. Especially for primary and junior doctors, the methods and systems of the present disclosure provide effective guidance and education, and improve their diagnostic accuracy. The present disclosure uses artificial intelligence assistance and image tracking to delineate and quantify lesion features, realize lesion analysis and generate structured electronic reports in seconds, thereby reducing workload and improving work efficiency of physicians and radiologists.

It should be noted that the above-mentioned steps are not necessarily performed in a particular. It is understood by those of ordinary skill in the art, based on the description of the embodiments of the present disclosure, that the above steps can be performed in various orders in different embodiments (e.g., in parallel or interchangeable).

In an embodiment, the medical image-based diagnostic report generation system may include a memory, a processor, and a computer program stored in the memory and runnable on the processor. When the computer program is executed by the processor, the following steps are performed: acquiring and displaying of a medical image of a subject; delineating a suspected lesion area in the medical image to generate a lesion-delineated area; quantifying features of the lesion-delineated area; analyzing the quantified features by AI technology and generating prompt information; indexing a pre-set expert index database according to the prompt information and generating a structured diagnostic report; and sending the diagnostic report to a physician for the physician to complete drafting of the diagnostic report.

The specific implementation steps are identical to those in the aforementioned embodiments and are not to be repeated herein.

Optionally, the computer program, when executed by a processor, may also implement the following steps: acquiring physician's instructions of a suspected lesion area; and performing close-loop delineation on the suspected lesion area according to the physician's instructions.

The specific implementation steps are identical to those in the aforementioned embodiments and are not to be repeated herein.

Optionally, the computer program, when executed by a processor, may also implement the following steps: acquiring a click command from the physician on a target area in the medical image; and delineating the target area to generate the lesion delineated area. Prior knowledge of the consistency of density features in surrounding areas may be used to generate the delineated area.

The specific implementation steps are identical to those in the aforementioned embodiments and are not to be repeated herein.

Optionally, the computer program, when executed by a processor, may also implement the following steps: obtaining a pre-trained model for identifying multiple disease; inputting a medical image into the AI model; and generating lesion-delineated areas based on the input.

The specific implementation steps are identical to those in the aforementioned embodiments and are not to be repeated herein.

Optionally, the computer program, when executed by a processor, may also implement the following steps: analyzing the lesion-delineated area on a single annotated layer based on the continuity of layers and lesion features in the medical images; and delineating similar lesion areas by automatically tracking n consecutive layers above and below the annotated layer, wherein n is a positive integer.

The specific implementation steps are identical to those in the aforementioned embodiments and are not to be repeated herein.

An embodiment of the present disclosure provides a non-volatile computer-readable storage medium. The computer-readable storage medium stores computer-executable instructions, which when being executed by one or more processors, may perform the steps S100-S600 in FIG. 13 as described above.

As examples, the non-volatile storage media may include read-only memory (ROM), programmable ROM (PROM), electrically programmable ROM (EPROM), electrically erasable ROM (EEPROM), or flash memory, Volatile memory may include random access memory (RAM) as external cache memory. By way of illustration and not limitation, RAM may be available in many forms, such as synchronous RAM (SRAM), dynamic RAM, (DRAM), synchronous DRAM (SDRAM), double data rate SDRAM (DDR SDRAM), enhanced SDRAM (ESDRAM), Synchlink DRAM (SLDRAM) and direct Rambus RAM (DRRAM). The disclosed memory components or memories of the operating environment described in the embodiments of the present disclosure are intended to include one or more of these and/or any other suitable types of memory.

Example 1

Training Image Dataset

A large and diverse training image dataset was assembled from a study cohort that includes 310,333 adult CXR images retrospectively collected from several publicly available datasets. These CXR images were acquired from multiple sources or hospitals around the world including those in USA, China, Belarus, etc. for different study or application purposes including NIH/TB Portal (https://tbportals.niaid-.nih.gov/) and MIMIC-CXR projects (https://physionet.org/content/mimic-cxr/2.0.0/). After collecting these CXR images, a panel of 8 radiologists who had 7 to 30-year experience in reading and diagnosing CXR images were assembled to retrospectively review and interpret these images based on clinically validated international medical terminology described and defined in Medical Dictionary for Regulatory Activities (MedDRA) UMLS CUI coding and/or Radiopaedia (http://radiopaedia.org). Each CXR image was first independently read by 3 radiologists and a consensus discussion followed if inter-reader variability in interpreting that image was detected. Then, the result confirmed by all 3 radiologists is used as "ground-truth."

Based on the confirmed results, 67,071 CXR images were normal images without abnormalities being detected, while in the rest of 243,262 CXR images, 307,415 regions of interest (ROIs) are detected and annotated, which represent 65 different types of lung abnormalities compliant with MedDRA terminologies. For example, 71,134 pneumonia ROIs were detected and marked on 54,582 CXR images. Among the top 20 types of abnormalities, 7 had more than 10,000 ROIs and 13 had more than 1,000 ROIs, while in the rest of 45 different abnormalities, 23 had more than 100 ROIs and 22 had less than 100 ROIs. Specifically, the distribution of the detected and marked abnormal ROIs among the top 20 abnormalities was: 22% of normal cases, 18% of pneumonia, 12% of secondary pulmonary tuberculos, 9% of hardening of the arteries, 9% of calcification, 8% of fibrogenesis, 5% of nodule, 5% of pleural thickening, 2% of tuberculous fibrosis of lung, 2% of rib fracture (staleness), and 8% of other diseases or abnormalities.

Smart Imagery Framing and Truthing (SIFT) System

The SIFT system consists of two networks namely, (1) a convolutional neural network (CNN) that aims to generate a detection, finer-grained segmentation and prediction score for each detected abnormal ROI based on Mask R-CNN framework, and (2) a multi-layer perception neural networks to fuse the results to generate the optimal recommendation for each image and each detected ROI based on decision fusion framework. The detailed architecture of the SIFT system is shown in FIG. 2. A Mask R-CNN network is augmented with a Feature Pyramid Network (FPN) to develop the SIFT system, which includes a top-down architecture with the lateral connections developed for building high-level semantic feature maps at all scales.

Generation of Diagnostic Report

Since the SIFT system is trained using 66 categories of CXR images (normal and 65 different abnormalities), its final output layer includes 66 nodes representing 66 categories. Based on the system-generated probability or likelihood scores of all identified and delineated ROIs depicted on the CXR image, the SIFT system also automatically generates several recommended abnormalities for a physician to select. Once the radiologist selects SIFT system-recommended abnormalities or diseases, the SIFT system automatically fills in semantic expression of the selected abnormalities in the diagnostic report and the corresponding descriptions. Various sentences have been created except that the disease/abnormality fields would be filled based on radiologist's selection. As a result, this can help increase efficacy of radiologists to write the final diagnostic reports.

Testing Image Dataset

In order to objectively evaluate the performance and potential clinical utility of the SIFT system, a second study cohort, which includes 22,642 CXR images that were prospectively collected from 54 hospitals widely spread in both urban and rural regions of Qinghai Province, China, during Aug. 17, 2021 to Nov. 17, 2021, were assembled. The CXR images in this cohort are used as an independent testing dataset. After all of these CXR images were collected and saved into our computer system, the same panel of 8 radiologists was invited to retrospectively review these images. Among them, the most senior (30 years of experience) served as study chair and the rest of seven served as study team members. Each study team member had a similar amount of workload (in terms of number of cases read) and the study chair performed image reading as well as judge. Using the same image review and reading protocol, each CXR image was independently read and interpreted by 3 radiologists to detect all lung abnormalities depicted on the image. These 3 radiologists were assigned randomly based on a fair workload. If inter-reader variability was detected, a consensus discussion led by the most senior radiologist with assistance of another senior radiologist, not involved in the initial detection, was followed to make the final decision.

As a result, 6,646 abnormalities or ROIs were detected and annotated on 4,068 CXR images, which represent 4 different types of abnormalities. In this testing dataset, approximately 18% of CAR images were identified as abnormal and 82% were normal. Specifically, 74% were normal, 9% were secondary pulmonary tuberculosis, 4% were pneumonia, 2% were calcification, 2% were pleural thickening, 2% were nodule, 1% was hardening of the arteries, 1% was rib fracture (staleness), 1% was pleural effusion, and 2% were other diseases or abnormalities.

Evaluation

Figure 18:
FIG. 18 shows the graphical user interface (GUI) of the SIF T system in accordance with an embodiment of the present disclosure.

The pre-trained SIFT system "as is" was applied to process each CXR image in the testing dataset, detect and segment suspicious ROIs, and generate diagnostic recommendations. As shown in FIG. 18, the graphic user interface (GUI) of the SIFT system includes an image report panel (in the middle as denoted by 1) that outlines the boundary contour of the detected and segmented abnormal ROIs, and a text report panel (on the right as denoted by 2) that reports classification recommendation with 3 confidence levels, low (L), middle (M), high (H), and presents automatically generated diagnostic description or report (on the right as denoted by 2). The SIFT system-generated detection, segmentation, and diagnostic recommendation results were reviewed by radiologists without viewing their original detection and annotation results. The radiologists were allowed to either directly accept SIFT system-generated diagnostic recommendation results or make any correction to the system-recommended results.

After collecting above study data, the overlap of ROIs annotated by radiologists and segmented by the SIFT system was compared to determine the true-positive, false-positive and false-negative ROIs detected by SIFT system. Second, since SIFT system has 66 output nodes with probability scores (i.e., prediction scores $0 \leq S_j \leq 1$, $j=1,2, \ldots, 66$), the system can make multiple recommendations of abnormalities sorted by the generated probability scores, which are greater than the prediction threshold. The acceptance rates of radiologists to accept different recommendations made by the SIFT system were analyzed. For example, what is the acceptance rate of the radiologists to accept the first recommendation (with the highest probability score).

Third, the receiver operating characteristic (ROC) type statistical data analysis method was applied to evaluate the performance of the SIFT system when applying it to the independent testing dataset. In order to mimic three popular scenarios in clinical practice, three different types of ROC data analyses in which the image cases are divided into positive and negative classes differently were performed. Specifically, the testing images were divided using three criteria namely, the specific abnormality vs. normal and all other abnormalities (screening scenario), the specific abnormality vs. normal cases (clinical scenario), and the specific abnormality vs. other abnormality cases (differential diagnosis scenario). The area under ROC curve (AUC) was used as the criterion to evaluate the performance of the SIFT system.

Performance at ROI Level

Figure 19:
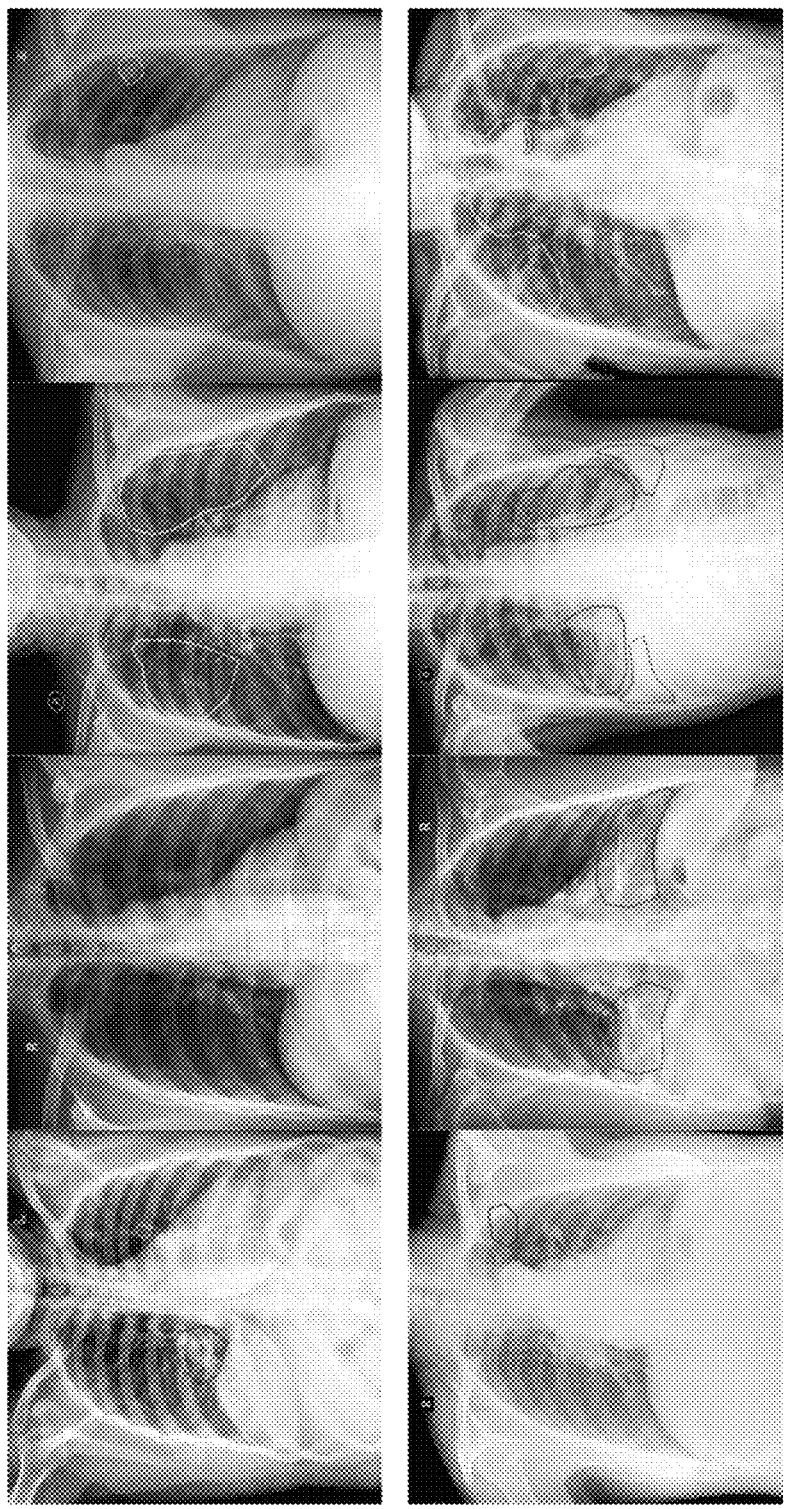
FIG. 19 shows exemplary CXR images analyzed and annotated by the SIFT system in accordance with an embodiment of the present disclosure.

As shown in FIG. 19, several CXR image examples in which the SIFT system-segmented boundary contour of different abnormalities (ROIs) are marked. Compared with radiologists' consensus detection results ("ground-truth"), the SIFT system detected 6,009 true-positive ROIs and 6,379 false-positive ROIs. However, 647 ROIs annotated by radiologists were not detected by the SIFT system. Thus, the SIFT system-detected results correspond to 90.3% (6,009/6,646) sensitivity and 0.28 (6,379/22,642) false-positive ROIs per image. In addition, the SIFT system did not detect false-positive ROIs in 38.4% of normal images.

Figure 20A:
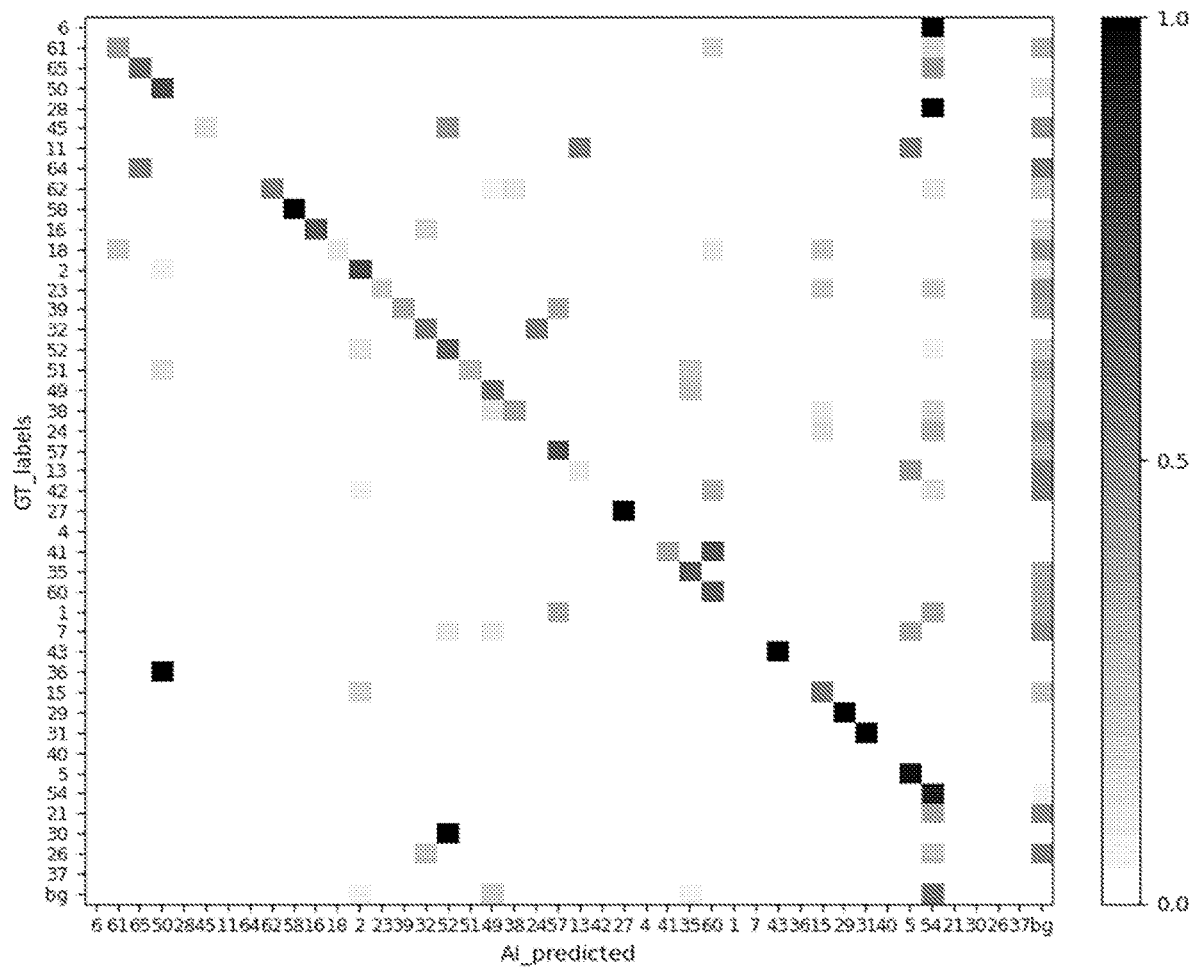
FIG. 20A shows a confusion matrix of radiologists in detecting different abnormalities without the assistance of the SIFT system in accordance with an embodiment of the present disclosure.
Figure 20B:
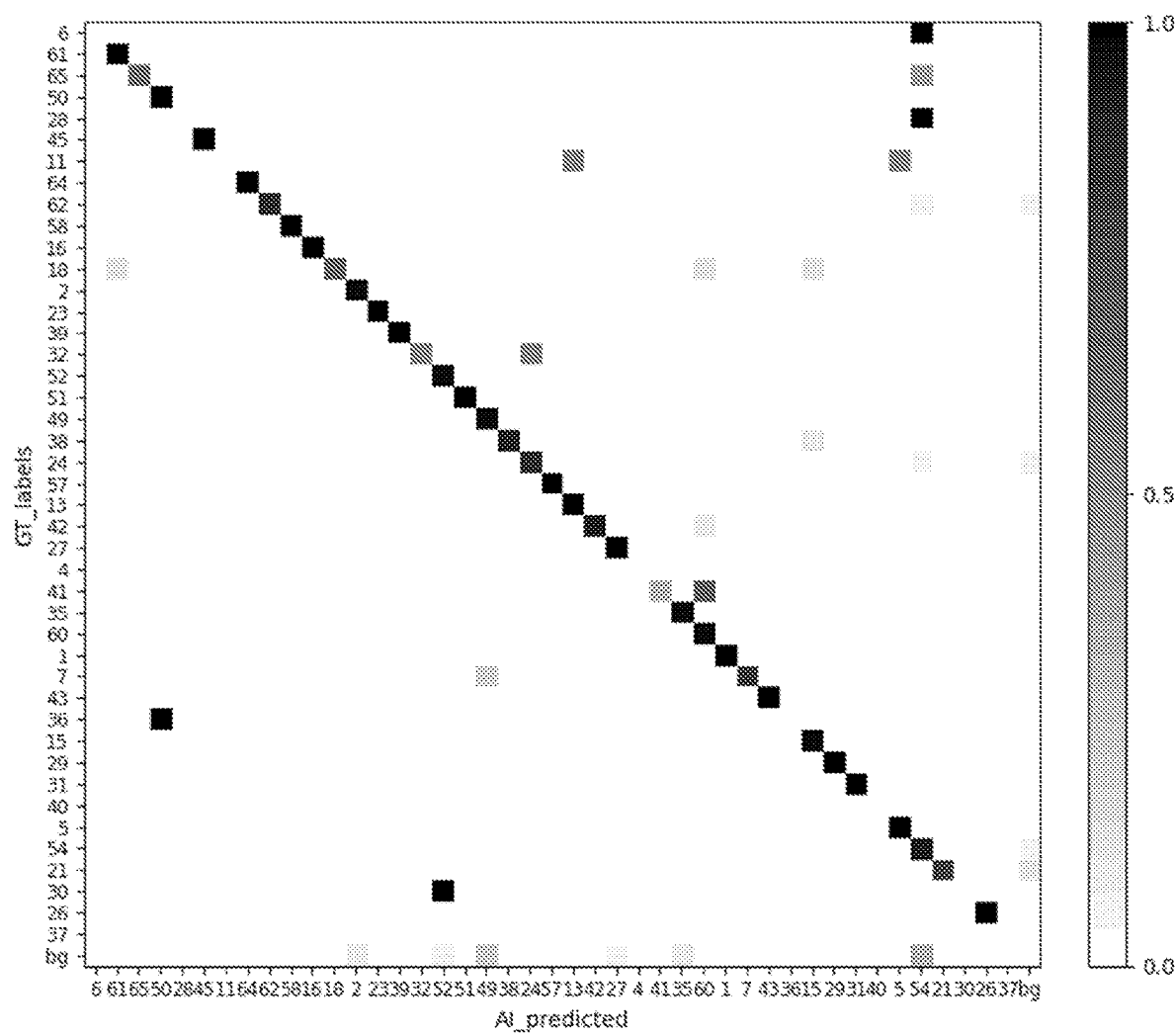
FIG. 20B shows another confusion matrix of radiologists in detecting different abnormalities with the assistance of the SIFT system in accordance with an embodiment of the present disclosure.

Referring to FIGS. 20A and 20B, which show two confusion matrix type distribution boxes that indicate the accuracy of radiologists in detecting 43 different types of abnormalities without using the SIFT system (as in FIG. 20A) and using the assistance of SIFT system (as in FIG. 20B), respectively. In these confusion matrix-based boxes, the density values of the squares along the diagonal line represent true-positive detection rate or sensitivity (from 0 to 1 or 100%), while the density values of other squares indicate error rates of the detection (e.g., abnormality 4 is detected as abnormality 5, etc.). Comparison between FIGS. 20A and 20B showed that radiologists yield higher detection sensitivity with the assistance of SIFT system, as indicated by the much darker color of the squares along the diagonal of FIG. 20A as compared to FIG. 20B. Comparing the off-diagonal squares in the two confusion matrices, there are more squares with relatively darker color in FIG. 20A than in FIG. 20B. This indicates that without the assistance of the SIFT system, higher detection error rates (including false-positive rates) were generated.

Figure 21:
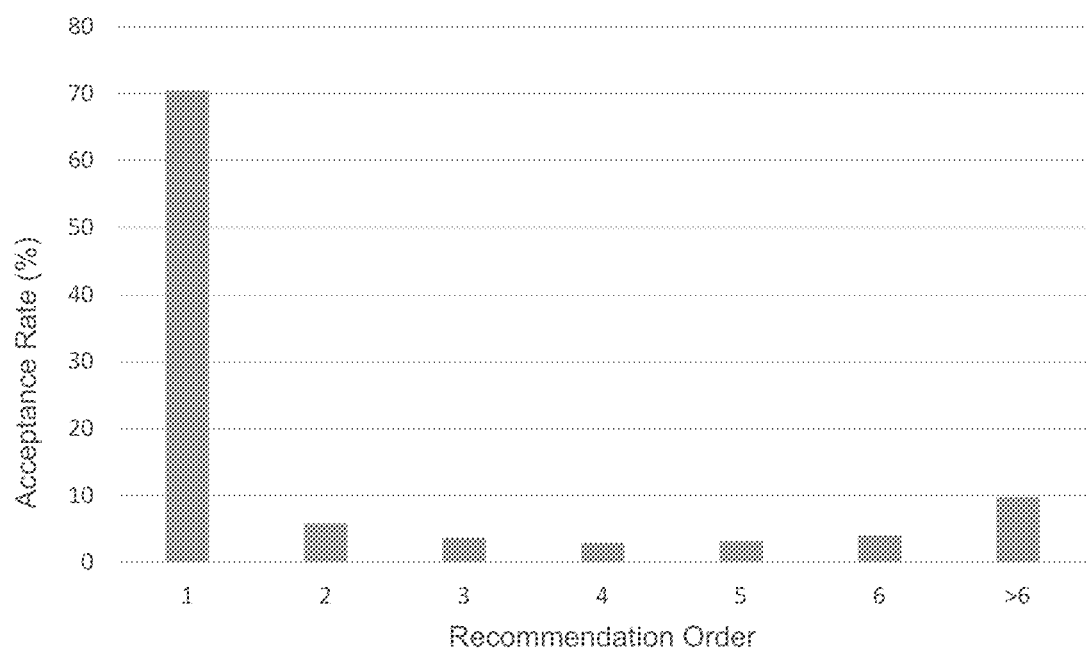
FIG. 21 shows acceptance rate by radiologists of recommendations generated by the SIFT system in accordance with an embodiment of the present disclosure.

Referring to FIG. 21, which shows a graph including 7 bars that indicate the acceptance percentage rates of radiologists in accepting the SIFT system-generated diagnostic recommendations. Specifically, in 70.4% of the detected true-positive ROIs, the radiologists accepted the first recommendation generated by the SIFT system. Thus, the SIFT system-generated diagnostic report can be directly used by radiologists. If radiologists select another SIFT system-generated recommendation, such as in 5.84% and 3.76% of the detected ROIs, radiologists select the second and third recommendation of abnormality type, respectively, the system can also automatically update the diagnostic report that can be directly adopted by the radiologists.

Performance at Image Level

The testing dataset included 43 different types of lung abnormalities. However, the numbers of different abnormalities vary significantly from 5 to more than 1,540. For detecting most abnormalities, AUC values were greater than 0.9. Only for 7 types of abnormalities, the AUC was smaller than 0.65, and five types only had five ROIs annotated. Table 1 below summarizes AUC values of 8 common lung abnormalities detected from CXR images in three disease detection scenarios. The AUC values range from 0.880 to 0.988, in which the lowest AUCs (0.880-0.914) and the highest AUCs (0.970-0.988) were achieved for detecting lung nodules and calcifications, respectively. For detecting secondary pulmonary tuberculosis, which had the largest number of cases in the testing dataset. At range from 0.958 to 0.987 in three detection scenarios. For example, in the screening scenario, sensitivity and specificity of detecting secondary pulmonary tuberculosis were 0.978 and 0.974, respectively. In other words, with the assistance of SIFT system, AUC values of detecting these 8 types of popular lung abnormalities in all three scenarios were significantly increased (p<0.001).

TABLE 1

| Type of Abnormality | Number of ROIs | Screening Scenario (95% CI) | Clinical Scenario (95% CI) | Differential Diagnosis Scenario (95% CI, P) |
|---|---|---|---|---|
| Secondary pulmonary tuberculosis | 1,540 | 0.984 (0.982-0.985) | 0.987 (0.985-0.989) | 0.958 (0.952-0.965) |
| Pneumonia | 813 | 0.959 (0.957-0.962) | 0.961 (0.959-0.96) | 0.944 (0.939-0.953) |
| Bronchitis | 18 | 0.976 (0.973-0.977) | 0.982 (0.959-0.964) | 0.949 (0.941-0.955) |
| Fibrous calcification | 62 | 0.972 (0.970-0.974) | 0.975 (0.973-0.977) | 0.959 (0.952-0.964) |
| Lung nodule | 398 | 0.909 (0.906-0.913) | 0.914 (0.911-0.919) | 0.880 (0.872-0.892) |
| Calcifications | 443 | 0.985 (0.984-0.987) | 0.988 (0.987-0.990) | 0.970 (0.967-0.977) |
| Mass | 18 | 0.914 (0.910-0.917) | 0.915 (0.911-0.919) | 0.906 (0.897-0.915) |
| Rib fracture | 181 | 0.960 (0.957-0.963) | 0.961 (0.958-0.963) | 0.956 (0.950-0.963) |

Figure 22:
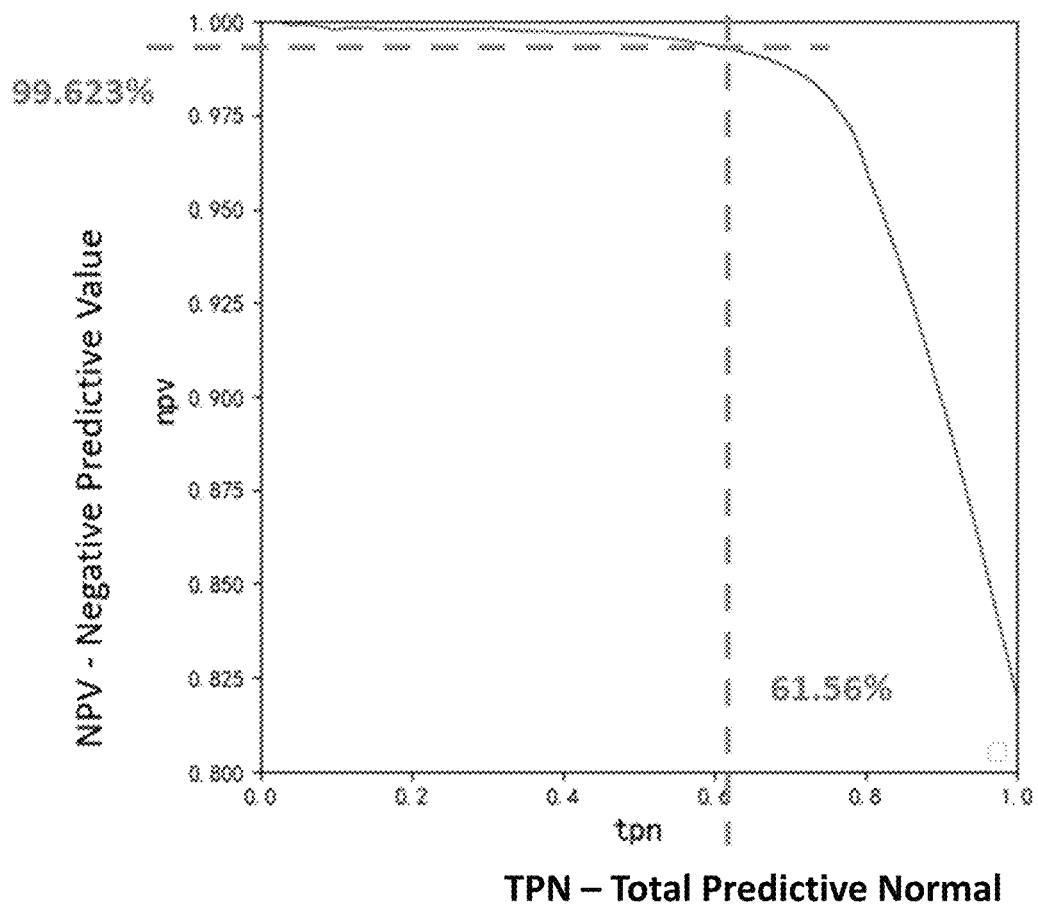
FIG. 22 shows an NPV-TPN plot of the SIFT system in accordance with an embodiment of the present disclosure.

The results shown in Table 1 can also be illustrated by ROC curves. The ROC curve (Receiver Operating Characteristic curve) is a graphical tool for evaluating the performance of a classifier. It can visualize the effect of classifiers and can compare different classifiers under different classification thresholds. As shown in FIG. 22, the ROC curve is drawn on the ordinate is the true positive rate (TPR) and the abscissa is the false positive rate (FPR). The TPR indicates the proportion of the samples that the classifier predicts as positive examples that are actually positive examples, while the FPR indicates the proportion of the samples that the classifier predicts as positive examples that are actually negative examples.

Vertical axis: True positive rate (TPR) can also be referred to as $$\text{sensitivity} = \frac{TP}{TP + FP},$$

Horizontal axis: False positive rate (FPR) can also be referred to $$(1 - \text{specificity}) = \frac{FP}{FP + TN},$$

Among, them, true positive (TP), false positive (FP), and true negative (TN) are concepts from the confusion matrix. TP represent the number of samples that are actually positive, and the classifier also predicts them as positive. TN represent the actual negatives, and the number of samples that the classifier also predicts as negative. FP represents the number of samples that are actually negative but are predicted to be positive by the classifier. False negatives (FN) represent the number of samples that are actually positive but are predicted to be negative by the classifier.

The area under the ROC curve (AUC) can also be used to measure the performance of the classifier. The larger the AUC, the better the performance of the classifier. When AUC=1, the classifier performs best, and when AUC=0.5, the classifier performs worst, which is equivalent to random guessing. AUC can also be used as an indicator to evaluate the ability of the model to separate positive and negative samples.

Figure 23:
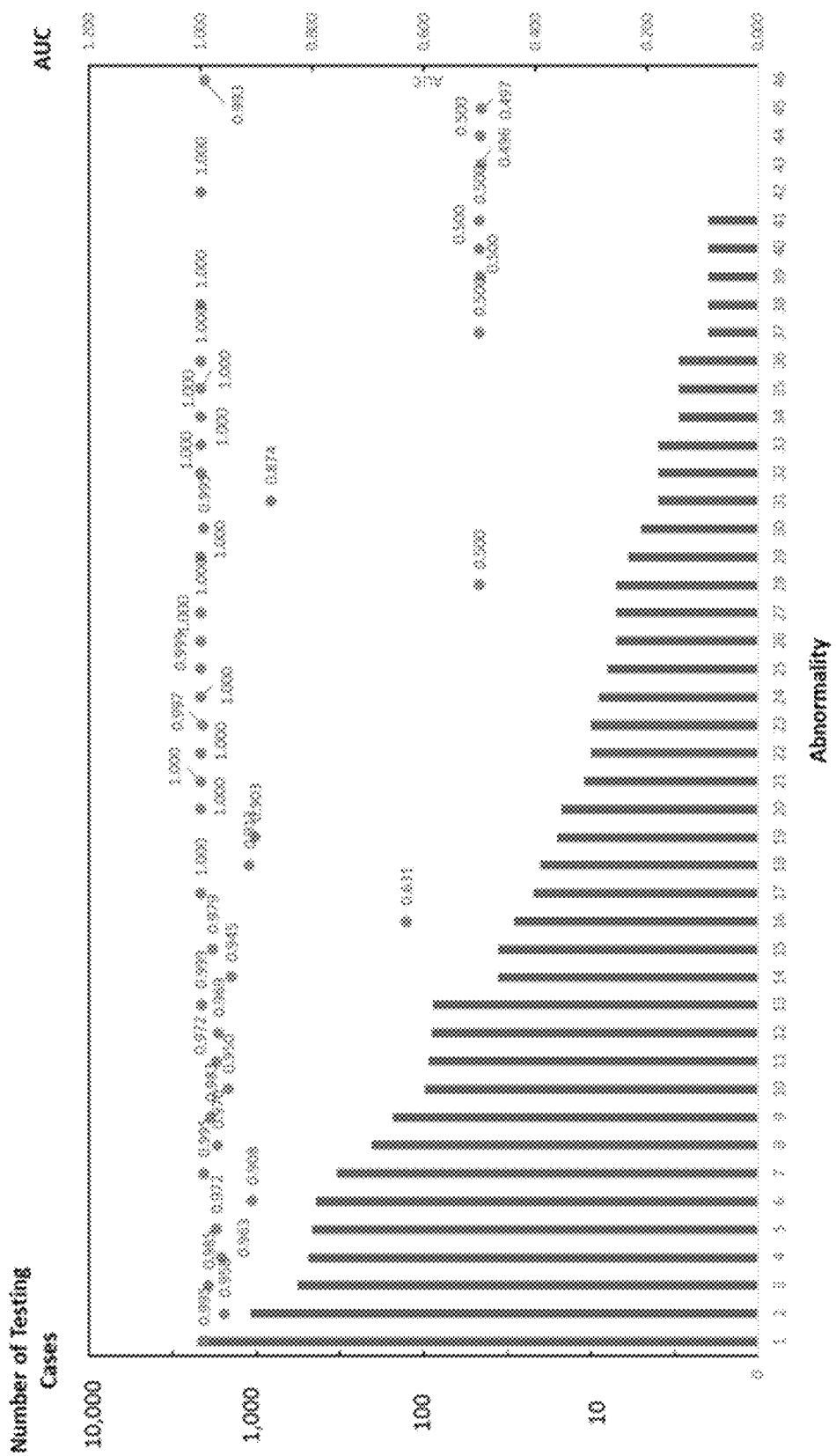
FIG. 23 shows a schematic diagram of the detection performance of the SIFT system in accordance with an embodiment of the present disclosure.

Referring to FIG. 23, which shows the detection performance of the SIFT system for each of 46 abnormalities. The abnormalities are listed in Table 2.

TABLE 2

| No | Abnormality |
|---|---|
| 1 | Secondary pulmonary tuberculosis |
| 2 | Pneumonia |
| 3 | Calcification |
| 4 | Fibrous foci |
| 5 | Pleural thickening and adhesions |
| 6 | Nodule |
| 7 | Aortic sclerosis |
| 8 | Rib fracture (old) |
| 9 | Pleural effusion |
| 10 | Fiber foci |
| 11 | Fibrous calcification |
| 12 | Postoperative changes |
| 13 | Chronic bronchitis and infection |
| 14 | Rib fractures |
| 15 | Bronchitis |
| 16 | Rib deformity |
| 17 | Pleural thickening, adhesion, calcification |
| 18 | Clumps |
| 19 | Pneumothorax |
| 20 | Enlarged thickened hilum |
| 21 | Pleurisy |
| 22 | Hematogenous disseminated pulmonary tuberculosis |
| 23 | Induration calcification |
| 24 | Atelectasis |
| 25 | Free gas under the diaphragm |
| 26 | Subcutaneous emphysema |
| 27 | Tuberculosis-lung destruction |
| 28 | Rib lesions |
| 29 | Heart disease-pulmonary congestion |
| 30 | Interstitial lung changes |
| 31 | Bullae |
| 32 | Pneumothorax |
| 33 | Interlobar pleurisy |
| 34 | Bronchiectasis and infection |
| 35 | Encapsulated pleural effusion |
| 36 | Emphysema |
| 37 | Clavicle fracture |
| 38 | Interstitial pneumonia |
| 39 | Lung contusion |
| 40 | Clavicle fracture (old) |
| 41 | Scapula fracture (old) |

TABLE 2-continued

| No | Abnormality |
|---|---|
| 42 | Heart disease-pulmonary congestion |
| 43 | Limited diaphragmatic dilatation |
| 44 | Lung cyst/bronchial cyst |
| 45 | Fibrous induration |
| 46 | Bronchiectasis |

As shown in FIG. 23, the SIFT system exhibited AUC larger than 0.5 for over 80% of the various abnormalities, including those having smaller numbers of testing samples.

Example 2

The SIFT system was trained with images containing 307,415 ROIs representing 69 different abnormalities and 67,071 normal CXRs. The SIFT system automatically labels ROIs with a specific type of abnormality, annotates fine-grained boundaries, gives confidence scores (i.e., prediction scores or probability scores), and recommends other possible types of abnormality. An independent set of 178 CXRs containing 272 ROIs depicting five different abnormalities including tuberculosis, pulmonary nodule, pneumonia, COVID-19, and fibrogenesis was used to evaluate radiologists' performance based on three radiologists in a double-blinded study. The radiologist first manually annotated each ROI without SIFT. Two weeks later, the radiologist annotated the same ROIs with SIFT aid to generate final results. Evaluation of consistency, efficiency and accuracy for radiologists with and without assistance of SIFT was conducted.

Figure 24:
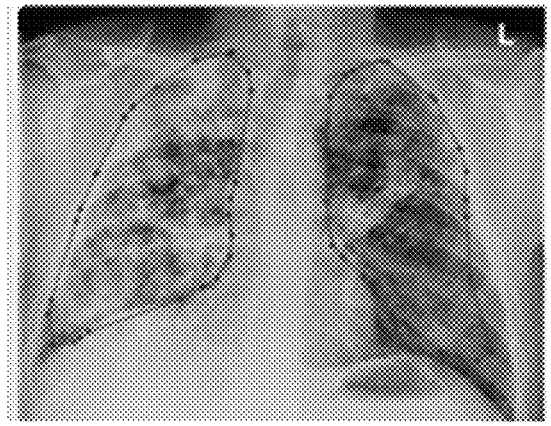
FIG. 24 shows exemplary CXR images annotated by radiologists and by the SIFT system in accordance with an embodiment of the present disclosure.
Figure 24:
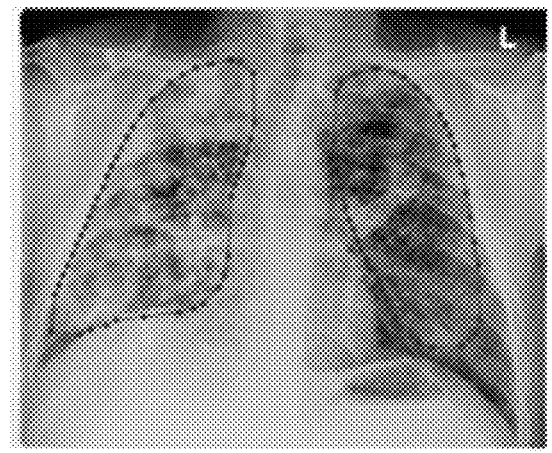
Figure 24:
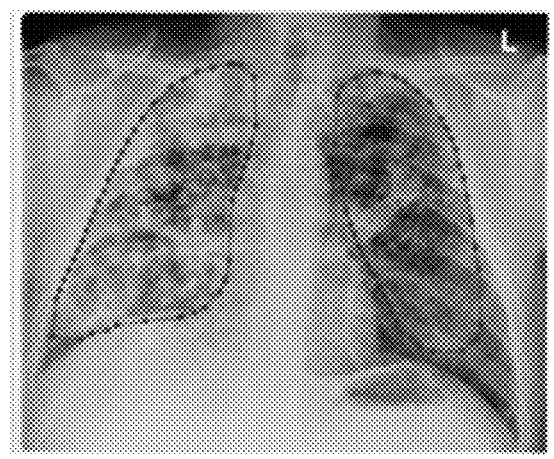
Figure 25:
FIG. 25 shows overlapped CXR images annotated by radiologist and by the SIFT system in accordance with an embodiment of the present disclosure.
Figure 25:
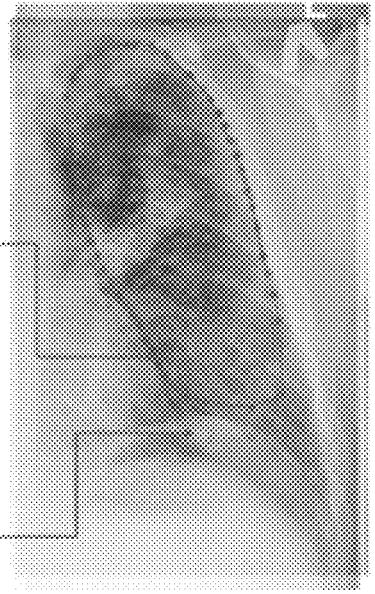

Referring, to FIGS. 24 and 25. After using the SIFT system, the radiologists accepted 9:3% SIFT annotated area. FIG. 24 shows an example of a tuberculosis (TB) image annotated by radiologists only (a), by the SIFT system only (b), and by radiologists using the SIFT system (c). FIG. 25 overlaps the images in FIG. 24 to demonstrate improvement of the radiologists in annotating ROIs with the assistance of the SIFT system.

Figure 26:
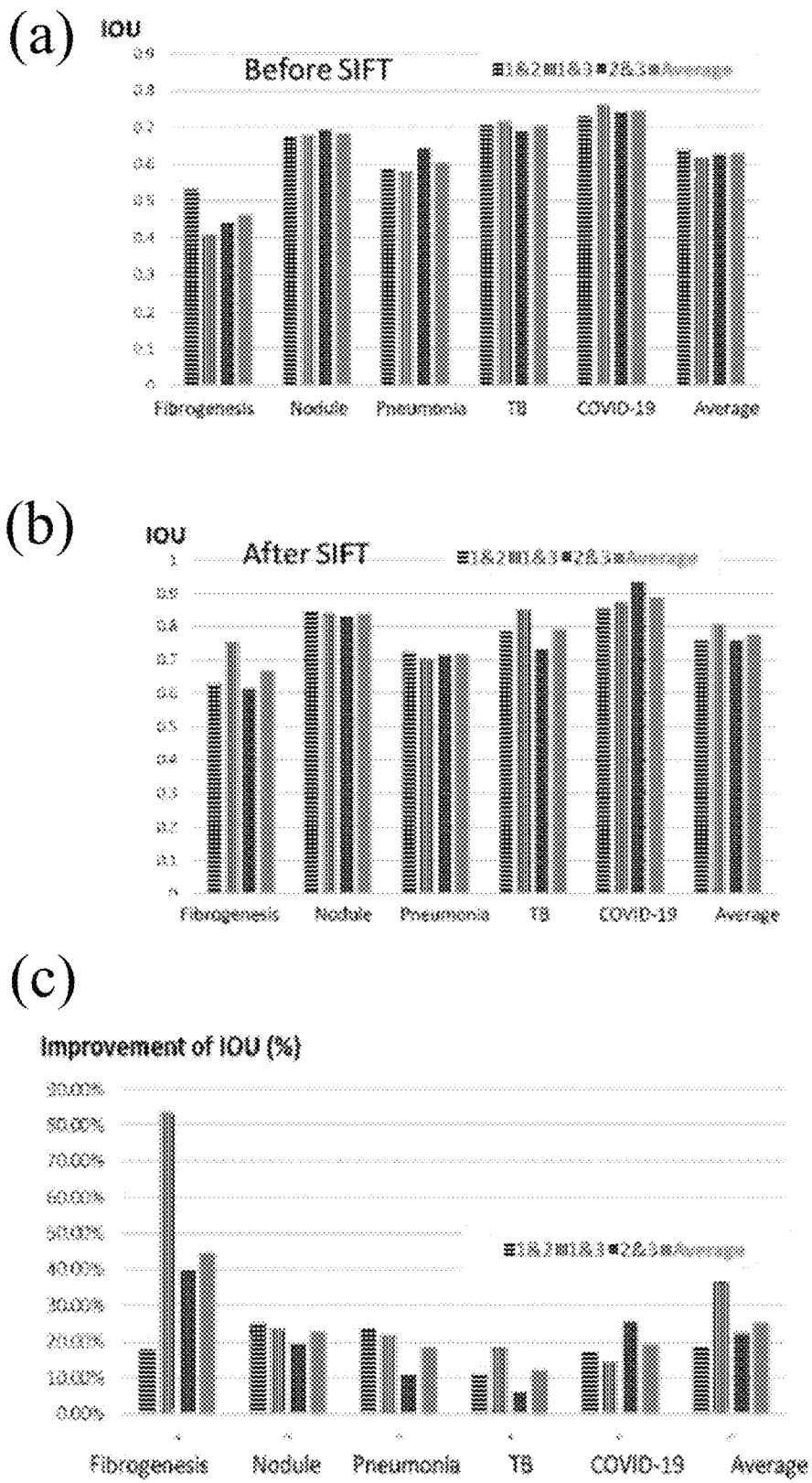
FIG. 26 shows the improvement of radiologists' performance with and without assistance of the SIFT system in accordance with an embodiment of the present disclosure.

Referring to FIG. 26, which shows the intersection over union (IOU) marked by two radiologists before using the SIFT system (a) and after using the SIFT system (b), as well as the improvement of IOU of the radiologists (c). As shown in FIG. 26, inter-observer variation improved by 25.27% on averaged IOU. Note that IOU improvement for radiologists before and after use of SIFT is the lowest for TB because the radiologists were very familiar with annotating TB.

Referring to FIG. 27, FIG. 28, and FIG. 29, which respectively show the consensus, annotation time, and performance among the radiologists in labeling ROI, with and without the assistance of the SIFT system. As shown in FIG. 29, variation across annotated area was reduced by 28.23%. The consensus true positive rate was increased by 5.00% (p=0.16), and the false positive rate was decreased by 27.70% (p<0.001). The radiologist's time to annotate the cases was decreased by 42.30%. Performance in labeling abnormalities statistically remains the same.

Results of the independent observer study showed that the SIFT system is a promising step toward improving the consistency and efficiency of annotation, which is important for improving clinical X-ray diagnostic and monitoring efficiency.

Advantages

The feasibility and clinical utility of the AI-based SIFT system of CXR images with several unique characteristics and contributions has been demonstrated. First, unlike conventional CAD schemes that focus on detecting a single type of abnormality (e.g., lung nodule) or disease (e.g., tuberculosis) or only detecting multiple types of abnormal images instead of ROI location, the embodiments of the present disclosure are the first multi-task CAD scheme that enables both "detection and finer-grained (pixel-wise) segmentation" of multiple lung abnormalities (up to 69 different abnormalities in current development phase). Additionally, the embodiments of the present disclosure are the first CAD scheme that automatically offer several recommended abnormalities instead of a single abnormality, when CAD prediction score for the first detected abnormality is not high enough or predicted abnormality may resemble others.

In order to increase transparency of the image processing and ROI segmentation results, the SIFT system is also integrated with a special custom-designed GUI display window that shows the location of the detected abnormality and the segmented boundary contour of the abnormality (as shown in FIG. 18). The GUI serves as a visual-aid tool aiming to increase confidence of the radiologists to consider and accept the system-generated, recommended diagnostic results in reading and interpreting CXR images. Also, the embodiments of the present disclosure are the first CAD system that not only perform interpretation on images but also automatically generate diagnostic text reports. Therefore, using the AI-based CAD scheme has potential to achieve higher clinical impact or add application value, particularly in the screening scenario including regular health or physical examination, which often results in the incidental detection of different types of lung diseases.

Second, the SIFT system has another unique AI function that enables automated drafting of the diagnostic report that describes characteristics and/or severity of the detected abnormalities. Such report drafting function has not been implemented in other existing CAD systems and evaluated in a large independent study cohort before. The SIFT system provides several diagnostic recommendations based on sorting the system-generated probability scores of the detected abnormalities. After a radiologist selects the correct recommendation using an easy computer mouse click action, the system can automatically update the diagnostic report that can be directly accepted as a final diagnostic report by the radiologist with minor revision or no revision. As demonstrated in FIG. 21, in 70.4% of the detected abnormalities, the first recommendation made by the SIFT system is directly accepted by the radiologists. As a result, it has been demonstrated that the SIFT system of the embodiments of the present disclosure helps increase efficacy of radiologists in reading and interpreting CXR images in clinical practices.

Third, since performance and scientific rigor of CAD schemes heavily depend on the image datasets, particularly for CAD schemes developed using deep learning technologies, which require "big data" of images, a much larger and diverse image dataset that includes 310,333 adult CXR images acquired from multiple sources was assembled to train the deep learning models using a transfer learning concept. In addition, the state-of-the-art deep learning models was chosen as the transfer learning models in developing the SIFT system of the embodiments of the present disclosure. Due to the large size of the training image dataset, which can adequately cover heterogeneity of lung abnormalities depicted on CXR images, data augmentation method may not be required to artificially increase training image dataset size. These choices train the SIFT system of the embodiments of the present disclosure more accurately and robustly by significantly reducing or minimizing the risk of overfitting. The SIFT system as evaluated b another unseen, large and independent study cohort that contains 22,642 CXR images acquired from 54 hospitals including many local community hospitals. Therefore, more robust performance evaluation results were demonstrated.

In view of the foregoing, the method and system of the various embodiment of the present disclosure are uniquely designed and trained to detect multiple lung diseases or abnormalities simultaneously and generate various recommendations of abnormality for each ROI. Through a unique observer evaluation study using a large unseen study cohort as an independent testing dataset, the SIFT system has been demonstrated to automatically (1) detect different types of lung abnormalities with high performance (i.e., AUC>0.9 for detecting most common lung abnormalities) and (2) generate diagnostic reports that can be directly accepted by radiologists.

Although the present invention has been described in considerable detail with reference to certain preferred embodiments thereof, the disclosure is not for limiting the scope of the invention. Persons having ordinary skill in the art may make various modifications and changes without departing from the scope and spirit of the invention. Therefore, the scope of the appended claims should not be limited to the description of the preferred embodiments described above.

What is claimed is:

1. A computer-implemented method for detecting lung abnormalities, comprising:
   S1: acquiring a chest image of a subject;
   S2: labeling one or more regions of interest (ROIs) in the chest image;
   S3: segmenting a fine-grained boundary of each of the labeled ROIs;
   S4: generating a plurality of output matrixes for each of the segmented ROIs;
   S5: sorting a plurality of prediction scores obtained in the output matrixes, and generating a plurality of recommendations of potential abnormalities for each of the ROIs; and
   S6: outputting the recommendations,
   wherein the method is implemented by a smart imagery framing and truthing (SIFT) system comprising augmented mask regions with a convolutional neural network (Mask R-CNN) and a multi-layer perceptron neural network (MLPNN) coupled to the Mask R-CNN,
   the Mask R-CNN comprises a Feature Pyramid Network (FPN) for feature extraction, a Region Proposal Network (RPN) coupled to the FPN and for region proposals creation, and an ROI Network coupled to the FPN and the RPN and for box and mask prediction, and
   the MLPNN comprises a Data Fusion Center (DFC) for fusing the output matrixes to improve accuracy of the prediction scores, a Max-Predictive Network (MPN) coupled to the DFC and for determining abnormalities having a maximum prediction score, and an Optimal Recommendation Network (ORN) coupled to the DFC and the MPN and for generating the recommendations.

2. The method according to claim 1, wherein the FPN splits a feature map from a channel dimension, convolves the feature map to generate a plurality of sub feature maps, concatenates and adds the generated sub feature maps, weighting the added sub feature maps to obtain a weighted feature map.

3. The method according to claim 2, wherein the added sub features maps are weighted according to steps of:
   performing global pooling on an unweighted feature map to obtain a one-dimensional tensor containing global information;
   applying the one-dimensional tensor to two fully connected layers to obtain an attention tensor having a length identical to that of the one-dimensional tensor;
   activating a softmax function to convert the attention tensor into a probability distribution;
   weighting the unweighted feature map according to the probability distribution; and
   outputting the weighted feature map.

4. The method according to claim 1, wherein the RPN adopts a first focal loss function for reducing class imbalance and improving prediction accuracy of difficult samples in region proposal creation,
   the first focal loss function is represented by Equation I $$FL(pt)=-(1-pt)^\gamma \times \log(pt) \qquad (I),$$

wherein pt is a probability of correct prediction, and $\gamma$ is a hyperparameter for controlling shapes of the focal loss function.

5. The method according to claim 1, wherein the RPN is trained by randomly selecting a predetermined number of anchor boxes matched to each ground truth (GT) box as positive samples, thereby ensuring that samples with large ROI areas and samples with small ROI area have equal chances to be matched as the positive samples.

6. The method according to claim 1, wherein the ROI Network adopts a second focal loss function for reducing class imbalance and improving accuracy of bounding box coordination and segmentation in box and mask prediction, and
   the second focal loss function is represented by Equation II $$FL(pt)=-(1-pt)^\gamma \times \log(pt) \times gtweight \qquad (II),$$

wherein pt is a probability of correct prediction, $\gamma$ is a hyperparameter for controlling shapes of the focal loss function, and gtweight is an array of weights assigned to each of the potential abnormalities.

7. The method according to claim 1, wherein the ROI Network is trained by randomly selecting a predetermined number of positive sample proposals for each ground truth (GT) box, thereby ensuring that samples with large ROI areas and samples with small ROI areas have equal chances to be matched as positive samples.

8. The method according to claim 1, wherein the MLPNN is fine-tuned with error back-propagation learning for updating weights to improve prediction accuracy.

9. The method according to claim 1, wherein the SIFT system is trained according to steps of:
   determining the prediction score of an input image; and
   if the prediction score is greater than current accuracy of the Mask R-CNN, including the input image into training dataset of the SIFT system, or if the prediction score is smaller than the current accuracy of the Mask R-CNN, re-training the SIFT system using the input image with correct annotations.

10. The method according to claim 1, wherein the Step S5 comprises steps of:
    S5.1: fusing the output matrixes, each of which comprises the prediction scores $S_j$, each of the prediction scores is associated with one potential abnormality, wherein $0 \leq S_j \leq 1$, $j=1,2,\ldots,n$, n is a positive integer;
    S5.2: sorting the prediction scores in each of the output matrixes;

S5.3: selecting the output matrix having prediction scores greater than a prediction threshold;

S5.4: generating the recommendations of potential abnormalities according to the selected output matrix.

11. The method according to claim 1, wherein Step S5 further comprises: when one of the ROI is overlapped by more than 30% in area by another ROI, merging the boundaries of the two ROIs; selecting, between the two ROIs, a higher prediction score associated with each potential abnormality; adjusting the selected prediction score according to Equation III; and generating the recommendations according to the adjusted prediction score, $$S = \begin{cases} \frac{score}{T} * 0.5 & score \leq T \\ \frac{score - T}{T} * 0.5 + 0.5 & score > T \end{cases}, \quad (III)$$

wherein T represents an optimal threshold.

12. The method according to claim 1, wherein the step S2 is performed in response to a user's input.

13. The method according to claim 1, wherein the chest image comprises a plurality of image layers, and the Step S3 further comprises steps of:

S3.1 defining the image layer having the segmented boundary as a first base layer;

S3.2 determining lesion features within the segmented boundary;

S3.3 detecting two image layers immediately adjacent to the first base layer and having the lesion features;

S3.4 segmenting regions having the lesion features in the adjacent image layers;

S3.5 defining at least one of the adjacent image layers as a second base layer; and S3.6 repeating the Steps S3.2 through S3.4 until the lesion features are no longer detected in the adjacent image layers.

14. The method according to claim 1, further comprising:

receiving a user's selection of one or more of the generated recommendations; and concatenating semantic expressions associated with the selected recommendations to generating a diagnostic report.

15. The method according to claim 1, further comprising:

constructing a knowledge tree module associated with image features of various lung abnormalities;

obtaining image descriptions and conclusions of each of the ROIs; and concatenating the image descriptions and conclusions according to the knowledge tree module.

16. A smart imagery framing and truthing (SIFT) system for detecting lung abnormalities comprising a memory and at least one processor coupled to the memory, the memory having a computer program stored therein, wherein when the computer program is executed, the processor is controlled to perform the steps of claim 1.

17. A non-transitory computer-readable medium for detecting lung abnormalities, comprising a computer program stored therein, wherein when the computer program is executed, a device installing the non-transitory computer-readable medium is controlled to perform the steps of claim 1.

* * * * *